(12) United States Patent
Lai et al.

(10) Patent No.: US 10,134,489 B2
(45) Date of Patent: Nov. 20, 2018

(54) MEDICAL PAD AND A WETNESS REPORTING SYSTEM WITH SUCH A MEDICAL PAD

(71) Applicant: Convergence Systems Limited, Wanchai (HK)

(72) Inventors: Kin Yue Albert Lai, Wanchai (HK); Cheuk Kuen Kenny Chan, Wanchai (HK); Man Wai Law, Wanchai (HK); Kwok Wah Sit, Wanchai (HK); Ngai Yin Chan, Wanchai (HK); Siu Chong Tin, Wanchai (HK); Wai Kin Chan, Wanchai (HK); Tak Leung Siu, Wanchai (HK); Yick Ming Yeung, Wanchai (HK); Jerry Garrett, Wanchai (HK)

(73) Assignee: Convergence Systems Limited, Wanchai (HK)

( * ) Notice: Subject to any disclaimer, the term of this patent is extended or adjusted under 35 U.S.C. 154(b) by 0 days.

(21) Appl. No.: 14/875,809

(22) Filed: Oct. 6, 2015

(65) Prior Publication Data
US 2017/0098044 A1    Apr. 6, 2017

(51) Int. Cl.
*G06K 7/10* (2006.01)
*G16H 40/20* (2018.01)
(Continued)

(52) U.S. Cl.
CPC ............. *G16H 40/20* (2018.01); *A61F 13/42* (2013.01); *A61F 13/505* (2013.01); *A61G 7/05* (2013.01); *G06F 19/00* (2013.01); *G06K 19/0716* (2013.01); *G06K 19/0717* (2013.01); *G06K 19/0723* (2013.01); *G06K 19/07745* (2013.01); *G06K 19/07749* (2013.01); *G16H 40/63* (2018.01); *A61B 5/1115* (2013.01);
(Continued)

(58) Field of Classification Search
CPC ........ A61F 13/42; A61F 13/505; A61F 13/84; A61F 2013/15154; A61F 2013/424; G06K 7/00; G06K 19/00; G06K 19/0723; G06K 19/07745; G06K 19/07749; G06K 19/0716; G06K 19/0717; G16H 40/20; G16H 40/63; A61G 5/1115; A61G 7/05; A61G 7/05715; A61G 9/00; A61G 2203/30; A61G 2203/34; A61G 2203/70; A61G 2205/60; A61B 5/1115; A61B 5/6892
USPC ........................................... 235/375
See application file for complete search history.

(56) References Cited

U.S. PATENT DOCUMENTS 5,868,723 A    2/1999   Al-Sabah
6,325,066 B1 * 12/2001   Hughes ..................... A61F 5/48
                                                 128/885

(Continued)

*Primary Examiner* — Claude J Brown
(74) *Attorney, Agent, or Firm* — Renner, Kenner, Greive, Bobak, Taylor & Weber Co. LPA

(57) ABSTRACT

A medical pad includes a piece of substrate with a major surface and an electric circuit on the major surface, a sensor connected with the electric circuit for measuring the electrical resistance of the electric circuit, and a wireless data transceiver or a radio frequency identification (RFID) tag electrically connected with the sensor for receiving results of the measuring from the sensor for subsequent transmission. The system carries out real time self-calibration to adaptively monitor the condition of a medical pad even in the face of changing environment and changing material properties.

20 Claims, 37 Drawing Sheets

(51) Int. Cl.
  *A61G 7/05* (2006.01)
  *G06K 19/07* (2006.01)
  *G06K 19/077* (2006.01)
  *G16H 40/63* (2018.01)
  *A61F 13/505* (2006.01)
  *A61F 13/42* (2006.01)
  *G06F 19/00* (2018.01)
  *A61F 13/15* (2006.01)
  *A61F 13/84* (2006.01)
  *A61G 7/057* (2006.01)
  *A61G 9/00* (2006.01)
  *A61B 5/11* (2006.01)
  *A61B 5/00* (2006.01)

(52) U.S. Cl.
  CPC ............. *A61B 5/6892* (2013.01); *A61F 13/84* (2013.01); *A61F 2013/15154* (2013.01); *A61F 2013/424* (2013.01); *A61G 7/05715* (2013.01); *A61G 9/00* (2013.01); *A61G 2203/30* (2013.01); *A61G 2203/34* (2013.01); *A61G 2203/70* (2013.01); *A61G 2205/60* (2013.01)

(56) References Cited

U.S. PATENT DOCUMENTS

| | | |
|---|---|---|
| 6,559,772 B2 | 5/2003 | Zand et al. |
| 6,756,521 B1 | 6/2004 | Breitkopf |
| 7,977,529 B2 | 7/2011 | Bergman |
| 9,107,776 B2 | 8/2015 | Bergman |
| 2003/0067149 A1* | 4/2003 | Gray ................ B60R 21/01516 280/735 |
| 2003/0227386 A1* | 12/2003 | Pulkkinen ............ A61B 5/1113 340/573.1 |
| 2004/0036484 A1* | 2/2004 | Tamai .................... A61F 13/42 324/663 |
| 2004/0115994 A1* | 6/2004 | Wulff ................. H01R 13/2471 439/700 |
| 2008/0041792 A1* | 2/2008 | Crnkovich ............. A61F 13/42 210/739 |
| 2008/0278336 A1* | 11/2008 | Ortega ................. A61B 5/1113 340/573.5 |
| 2010/0072271 A1* | 3/2010 | Thorstensson ......... A61F 13/42 235/375 |
| 2010/0199901 A1* | 8/2010 | Kang ..................... A41D 27/00 112/439 |
| 2010/0308970 A1* | 12/2010 | Rofougaran ......... H01Q 1/2283 340/10.1 |
| 2013/0078299 A1* | 3/2013 | Harriton ................. A61K 9/06 424/443 |
| 2013/0143020 A1* | 6/2013 | Wood ................. A61F 13/0206 428/220 |
| 2014/0138259 A1* | 5/2014 | Mickelson ......... G01N 33/0044 205/775 |
| 2014/0144995 A1* | 5/2014 | Conner ............. G06K 19/07788 235/492 |
| 2014/0273899 A1* | 9/2014 | Dokai .................... H04B 1/525 455/180.1 |
| 2014/0275850 A1* | 9/2014 | Venkatraman ....... A61B 5/0002 600/301 |
| 2016/0078176 A1* | 3/2016 | Ranta .................. G06F 19/322 705/2 |

* cited by examiner

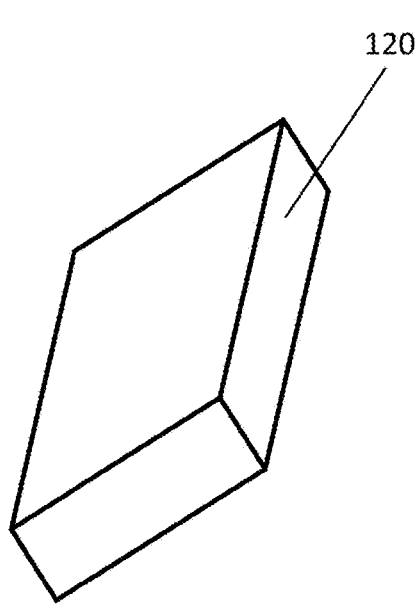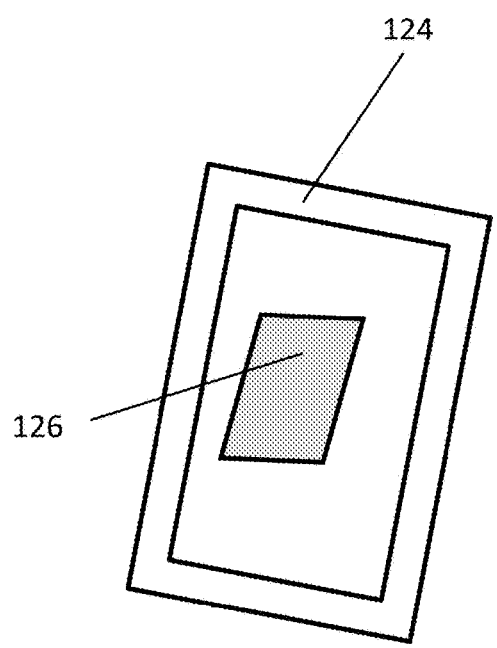
Fig. 26
Fig. 27

Metal backed plastic casing, using novel excitation design as in last figure
Original parallel plate travelling wave transmission line
*Fig. 36*
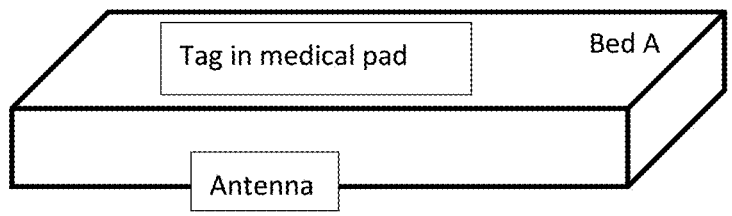
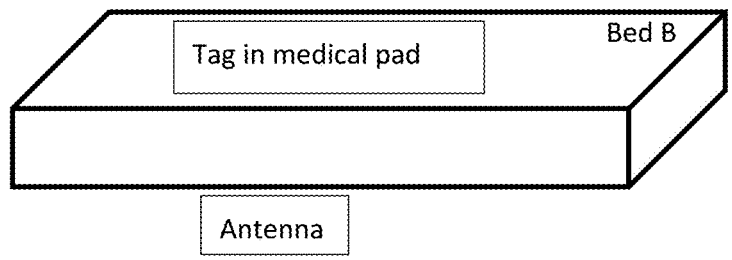
*Fig. 37*

Have you rolled over the following client yet?

| John Dole |
| West Wing |
| Room 2 |
| Bed 2 |

*Fig. 52*

Medical Pad Events and Nurse Actions Record of Client:

| John Dole | West Wing |
| Room 2 | Bed 2 |

| Pad Event | Nurse Action | Time | Sensor ID | Pad Signature |
| --- | --- | --- | --- | --- |
| | | | | |
| | | | | |
| | | | | |
| | | | | |
| | | | | |
| | | | | |

*Fig. 53*

MEDICAL PAD AND A WETNESS REPORTING SYSTEM WITH SUCH A MEDICAL PAD

TECHNICAL FIELD

This invention relates to a medical pad and a wetness reporting system incorporating such a medical pad.

BACKGROUND OF THE INVENTION

Incontinence refers to the involuntary excretion of urine or bowel contents by a person. This condition can happen when a person is in hospital, extended care facility, or home care environment. For some people, it is a short term condition, for example, right after medical operation in a post-anesthesia state. For some people, it is a medium term condition which may last for a few months, for example due to injuries. For some other people, it is a long term condition where the voluntary control of urinary tract or bowel is lost permanently. The incontinence condition will be particularly problematic for this last group of people if they are also unable to move because of paralysis, illness or old age.

Incontinence is a major contributing or aggravating factor for bed sores. Bed sores, or pressure ulcers, are injuries to skin and underlying tissue resulting from prolonged pressure on the skin. Prolonged pressure slows down blood flow to the skin and top layer of subcutaneous fat and muscle, and skin lesion will easily occur. When that happens, infection will arise if bacteria are allowed to go near. As a person lies on bed with the body underneath in a wet condition due to urine and/or bowel material (which contains a lot of bacteria), the skin of the person will become much more vulnerable to infection and therefore develop lesions much faster than if it is dry. It has been reported that bed sores can happen within one and a-half hour to two hours of staying on bed immobile. Once bed sores develop, it typically may take at least five additional days of hospital stay to treat it.

If the incontinent person lies on bed, a large rectangular medical pad is usually applied between the person and a mattress on which the person lies. A medical pad has two critical layers: a Super Absorbent Polymer (SAP) based water absorption layer, and a waterproof layer underneath the SAP layer. Using a medical pad, the moisture of any involuntary excretion can be absorbed with the primary purpose of keeping the person as dry as possible, and the secondary purpose of keeping the mattress clean and hygienic. If the mattress is messed up and cannot be effectively cleaned, it has to be cleaned or even replaced. Cleaning or replacing the mattresses is very expensive.

The existing medical pad, however, is not without shortcomings. For example, the existing medical pad cannot keep the person completely dry because there are crevices and parts of the body which are not in touch with the medical pad. Furthermore, the medical pad has its own maximum moisture capturing capacity, beyond which the person will still be wet. Since the medical pad is right underneath the patient, its wetness extent is not visible and the patient has to report the wetness to the nurse if the patient wants immediate relief or replacement of the medical pad. This is not always easy, especially for patients with reduced mobility or consciousness.

Because of this, a nurse still has to check the medical pad regularly to see if it is wet, and if wet, replaces it. To do the checking, the nurse needs to roll over the person and touch the medical pad to feel it and see if it is wet. The person, if sleeping, will often be woken up. In other cases, the person, with certain injuries to the body or the spine, may not fare too well with too many of these roll over actions. In fact, the roll over action itself, with the accompanying coldness felt by the patient as the back of the body is side way rolled away from the mattress, may actually become stimulation to the patient and cause the patient to become incontinent soon after the roll over event occurs.

Moreover, the nurse can only check the patient once in a while, with the time period longer or shorter depending on the availability of nurse resources in the hospital or extended care or home care facility. Therefore there will be a time lapse between the involuntary excretion and the time where the nurse will discover and replace the medical pad. Prolonged exposure to this wetness condition will aggravate or induce bed sores, technically known as pressure ulcers. Bed sore is very difficult to treat for bed-ridden persons, and causes major discomfort. In most cases, persons developing bed sores in hospital will cause an increase in total number of days of hospital stay—the extra days needed to medically treat this bed sore condition.

From 2015 onward, with the new Affordable Care Act in the US, if bed sores are acquired during the hospital stay, any extended hospital stay to treat bed sore is no longer covered by insurance. The hospital has to bear the cost of the extended stay.

General hospital practice to prevent bed sore is for the nurse to roll the patient over every two hours—this is assuming the patient is dry. If during this two-hour interval the patient becomes wet due to incontinence, then the aggravating effect of this wetness will make this two-hour "roll the patient" period not short enough. In fact, heavy incontinence can indeed happen in one or two hours, depending on the health situation and overall condition of the patient.

To overcome this, a better way is to have a medical pad that can sense this wetness and notify the nurse in a timely manner, so that the nurse can come to replace the pad. This will be a most useful device for incontinent persons, whether short term, medium term or long term.

Wetness detection or moisture monitoring has been around for many years. The earliest design consists of two wires 12, 14 or two printed conductive ink traces, as shown in FIGS. 1 and 2. Terminals of the two wires 12, 14 are connected to a resistance measurement device 16. When the area across the twin wires 12, 14 or traces is dry, as shown in FIG. 1, the electric circuit is an open circuit with a very high electrical resistance. When any area across the twin wires 12, 14 or traces is wet, and hence conductive, as shown in FIG. 2, the electric circuit is closed and the resistance becomes a lower finite value. A simple threshold will separate the open circuit and the closed circuit, and thus differentiates between dryness and wetness. This is the most basic design of wetness detection.

When one varies the width between the two lines 12, 14, one can control the sensitivity of the wetness detection. The wider the separation, the larger amount of liquid is required to short the circuit. This method is used for setting the sensitivity of the system to that desired by the user. Comparing the arrangement shown in FIG. 3 and that shown in FIG. 4, it can be seen that more liquid is required for electrically connecting the wires 12, 14 in FIG. 4 than for connecting wires 12, 14 in FIG. 3. In the case of medical pad, the nurse would certainly want to limit the warning or alert to happen only when the incontinence amount reaches a certain level. When there is only a very small amount of excretion, usually the medical pad can handle that. Only when the amount of excretion becomes so large that the medical pad can no longer effectively handle the situation, then the nurse has to come and replace the pad and also dry up the patient.

Using a twin-wire design to cover up a large rectangular area is possible, where one meanders a twin-wire 18 in a generally "Z" manner throughout the rectangular area, as shown in FIG. 5. This design has one flaw: the sensitivity of the area between the twin-wire 18 and the sensitivity of the area between two lengths of the meandering twin wire are different.

Other than the twin-wire design, a comb design, as shown in FIG. 6, is also very popular and has been around for many years. In this design, two terminals 20, 22 fan out to become each side of an interlocking pair of combs. In this design, the flaw of the twin wire design is overcome, where the sensitivity is the same throughout. This interlocking comb design, however, also has its own flaw. The ink printed trace has its own resistivity per length. As the trace travels down the comb farther and farther away from the incoming terminal 20, 22, the total resistance becomes larger and larger. This creates a problem in setting the threshold for wetness measurement.

It is thus an object of the present invention to provide a medical pad, a wetness reporting system and a method of reporting wetness of a subject in which the aforesaid shortcomings are mitigated or at least to provide a useful alternative to the trade and public.

SUMMARY OF THE INVENTION

According to a first aspect of the present invention, there is provided a medical pad including a piece of substrate with a major surface and an electric circuit on said major surface, a sensor connected with said electric circuit for measuring the electrical resistance of said electric circuit, and a data transmitter for receiving results of said measuring from said sensor for wireless transmission.

According to a second aspect of the present invention, there is provided a wetness reporting system including at least one medical pad, said medical pad including a piece of substrate with a major surface and an electric circuit on said major surface, a sensor connected with said electric circuit for measuring the electrical resistance of said electric circuit, and a data transmitter for receiving results of said measuring from said sensor for wireless transmission.

According to a third aspect of the present invention, there is provided a method of reporting wetness of a subject, including the steps of (a) positioning an electric circuit beneath said subject, (b) measuring the electrical resistance of said electric circuit, (c) wirelessly transmitting data indicative of the electrical resistance of said electric circuit, and (d) determining, on the basis of said data, whether the subject is wet.

According to a fourth aspect of the present invention, there is provided a method of calibrating a medical pad, wherein said medical pad includes a piece of substrate with a major surface and an electric circuit on said major surface, a sensor connected with said electric circuit for measuring the electrical resistance of said electric circuit, and a data transmitter for receiving results of said measuring from said sensor for wireless transmission, wherein said electric circuit includes a first electrically conductive line with a first terminal and a second electrically conductive line with a second terminal, each said electrically conductive line being in the shape of a comb and interlocking with each other, and wherein said electric circuit further includes a third terminal connecting with said second electrically conductive line via a calibration conductive line, said method including a step (q) of measuring the electrical resistance of said calibration conductive line.

BRIEF DESCRIPTION OF THE DRAWINGS

Embodiments of the present invention will now be described, by way of example only, with reference to the accompanying drawings, in which:

FIG. 26 shows an active sensor module according to the present invention;

FIG. 27 shows a docking area on a medical pad according to the present invention;

FIG. 36 shows hermetic sealing of the antenna of the sideway excitation arrangement of FIG. 35 and the antenna of the present invention;

FIG. 37 shows two beds each provided with a medical pad according to the present invention and an antenna;

FIG. 52 shows an exemplary pop up reminder window displayed in a wetness reporting system according to the present invention;

FIG. 53 shows an exemplary event and nurse action record window displayed in a wetness reporting system according to the present invention;

DETAILED DESCRIPTION OF THE EMBODIMENTS

Broadly speaking, a wetness reporting medical pad (or alternatively called an incontinence detecting medical pad) according to the present invention includes an active medical pad and a passive medical pad. It therefore follows that a wetness reporting system according to the present invention includes an active wetness reporting system and a passive wetness reporting system.

Figure 1:
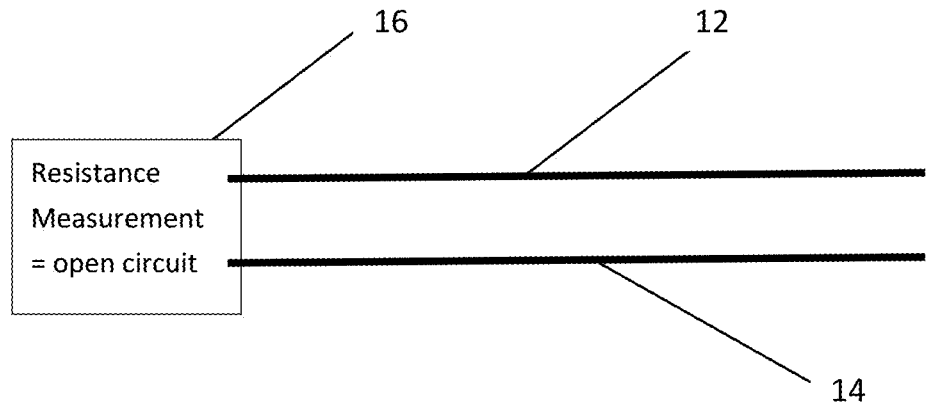
FIG. 1 shows a prior art wetness detection arrangement in an open-circuit configuration.
Figure 2:
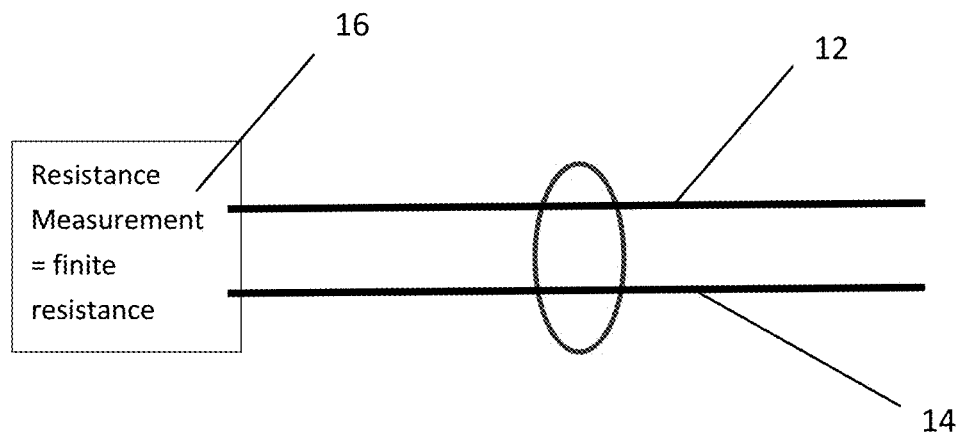
FIG. 2 shows the wetness detection arrangement of FIG. 1 in a closed-circuit configuration.
Figure 3:
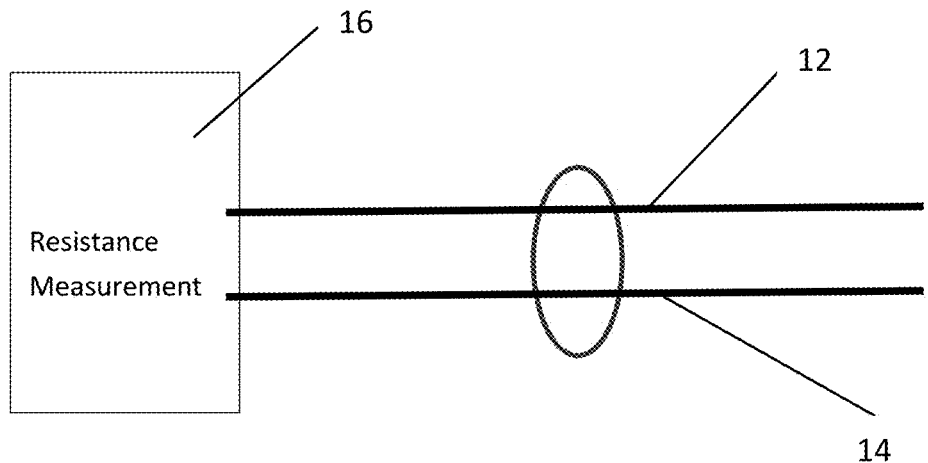
FIG. 3 shows the wetness detection arrangement of FIG. 1 with two electrically conductive wires separated by a first distance.
Figure 4:
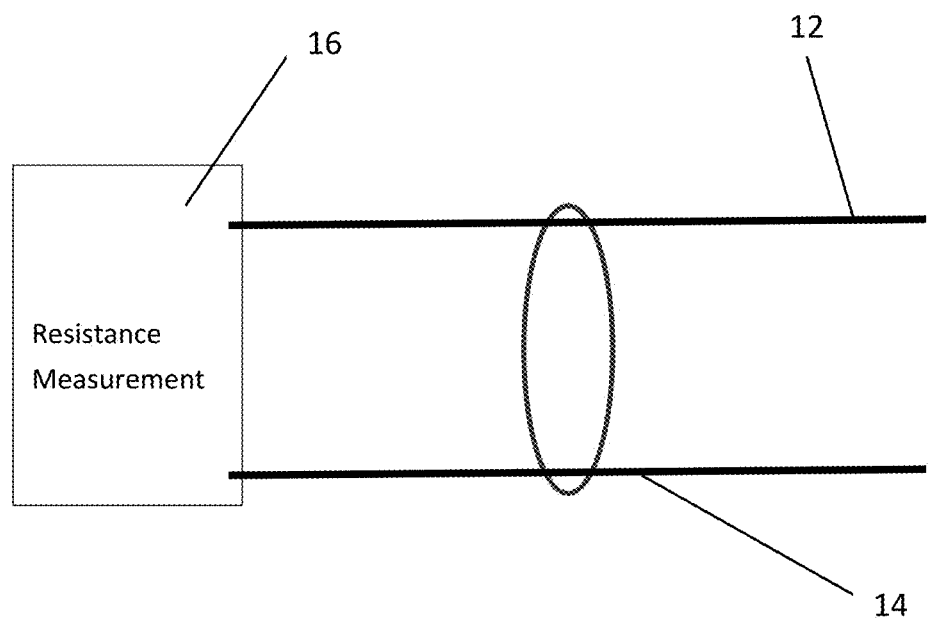
FIG. 4 shows the wetness detection arrangement of FIG. 3 with the two electrically conductive wires separated by a second, larger, distance.
Figure 5:
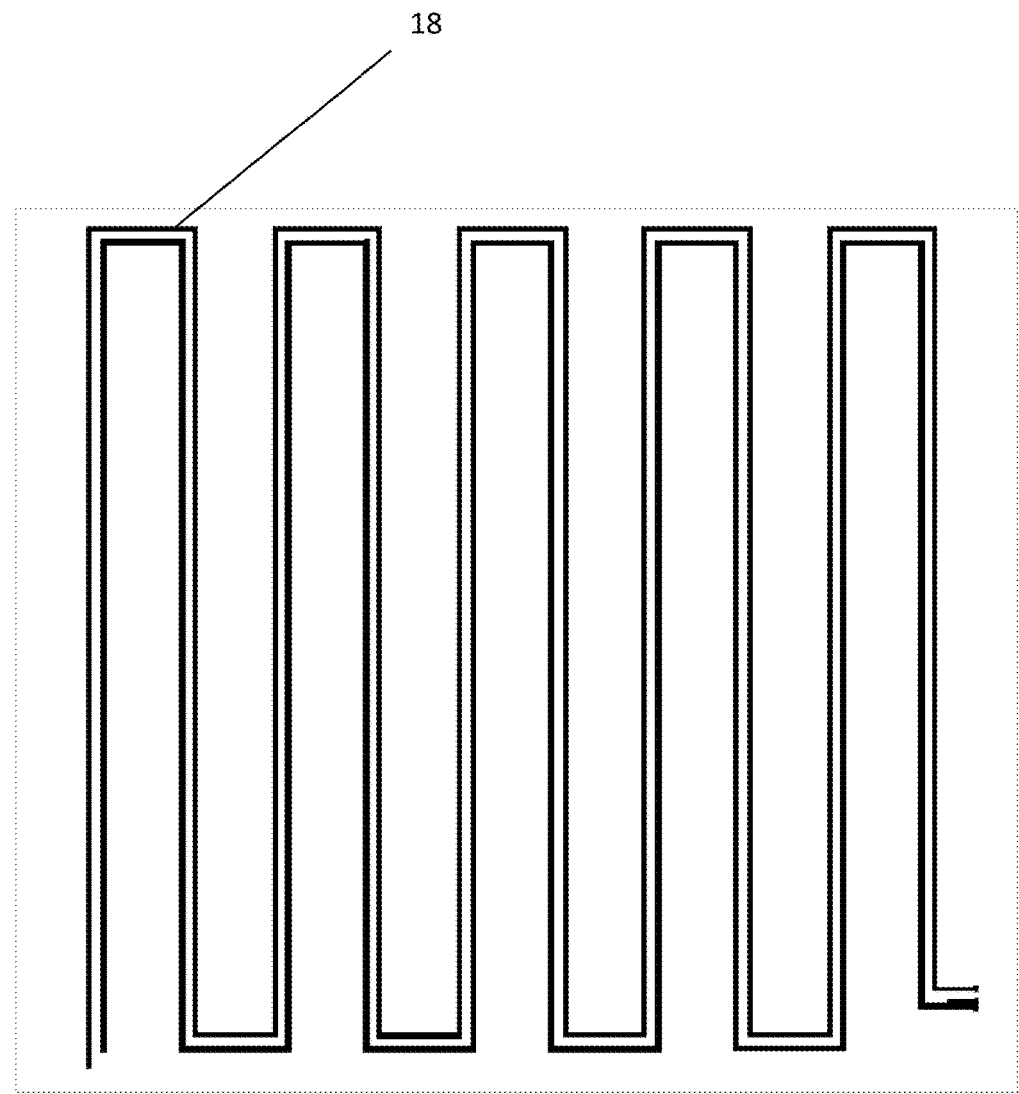
FIG. 5 shows a prior art twin-wire design of a wetness detection arrangement.
Figure 6:
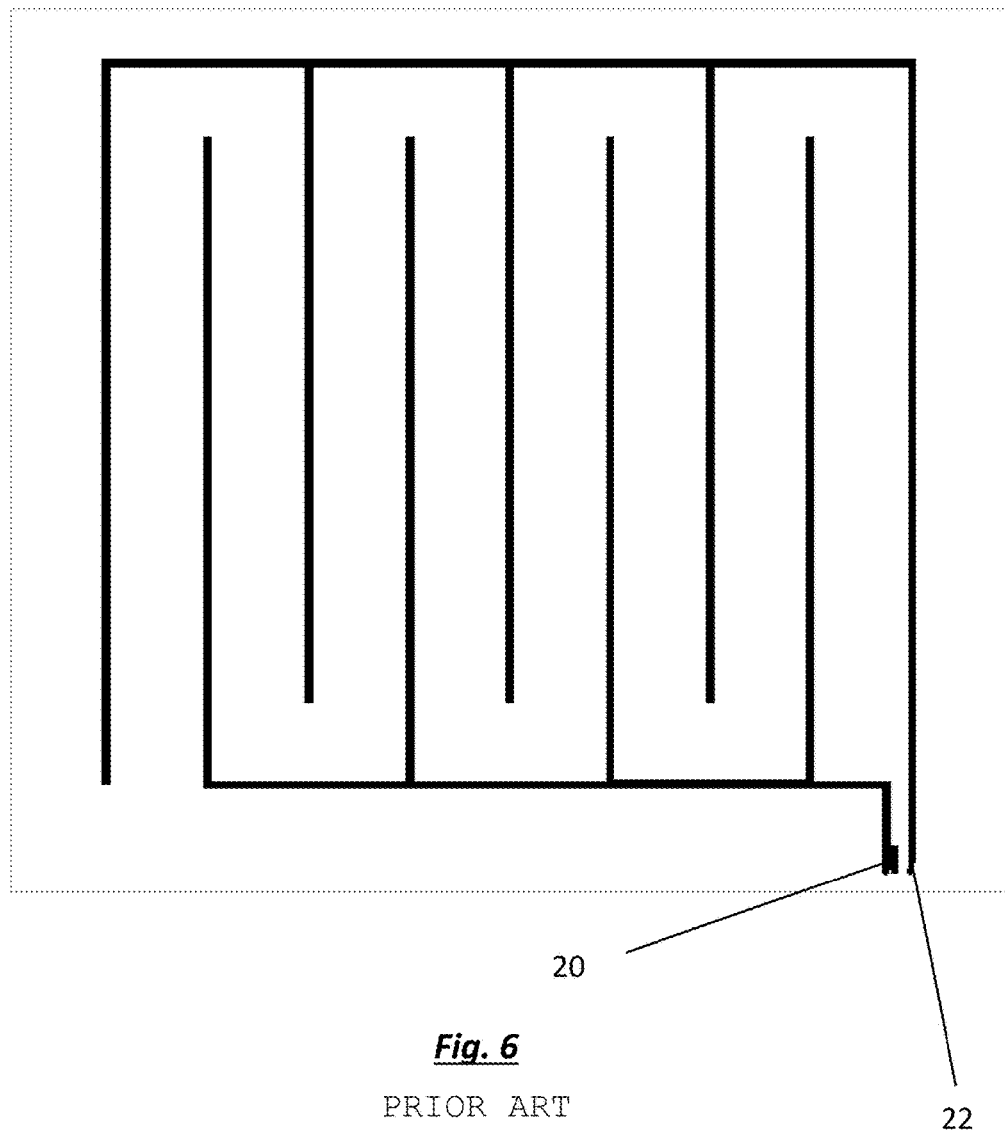
FIG. 6 shows a prior art comb design of a wetness detection arrangement.
Figure 7:
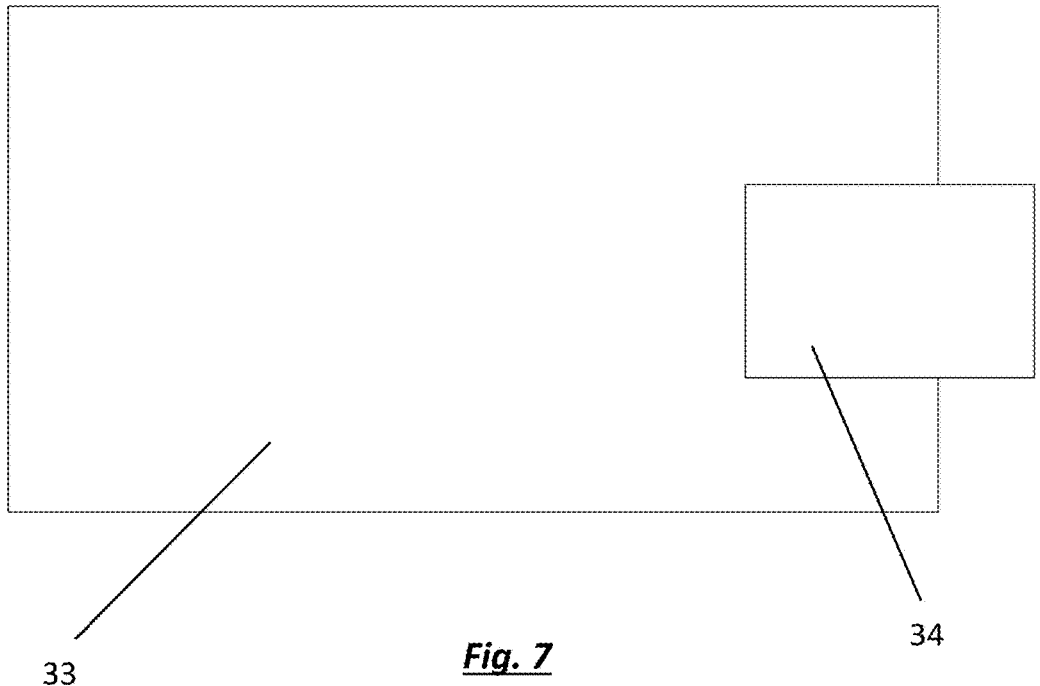
FIG. 7 shows a schematic diagram of an active incontinence detecting medical pad according to the present invention.
Figure 8:
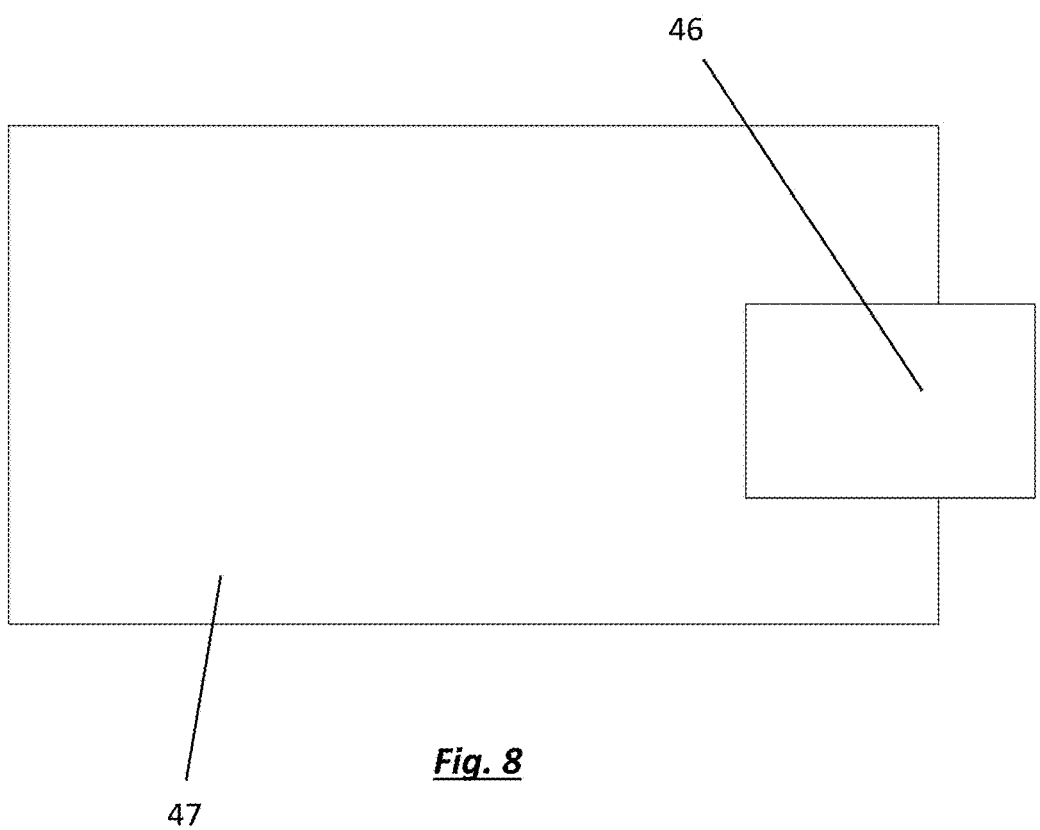
FIG. 8 shows a schematic diagram of a passive incontinence detecting medical pad according to the present invention.

Basically, the terms "active" and "passive" refer to whether an electric battery is provided on the medical pad. As shown in FIG. 7, an active wetness reporting medical pad 33 includes a wetness detection electric circuit and an active sensor module 34 that runs on battery power. The active sensor module 34 is an integrated circuit (IC), being both a sensor for sensing and measuring the electrical resistance of the wetness detection electric circuit and a wireless data transceiver. As shown in FIG. 8, a passive wetness reporting medical pad 47 includes a wetness detection electric circuit and a passive sensor module 46 with a passive RFID tag that does not require battery power. The passive RFID tag acts as both a sensor for sensing and measuring the electrical resistance of the wetness detection electric circuit and a wireless data transceiver.

The reason why the passive wetness reporting system can operate without battery power is that an ultra high frequency (UHF) RFID reader is used to wirelessly energize the passive RFID tag on the medical pad 47. Once energized, the passive RFID tag will perform wetness measurement, and the RFID reader will then be able to get the wetness measurement information from the passive RFID tag on the medical pad 47.

In the active wetness reporting system, the battery-powered active sensor module 34 on the medical pad 33 will periodically measure the wetness amount and send out wetness alert to a backend server. The measurement period is configurable and is typically set to be half a minute.

In a passive wetness reporting system, the RFID reader will periodically read the medical pad 47 and check for wetness. Although the medical pad 47 itself does not contain any battery, the wireless energy from the RFID reader is strong enough to energize the passive RFID tag in the medical pad 47 to do the wetness measurement. Again, this measurement period is configurable, and is typically set to one minute.

Figure 9:
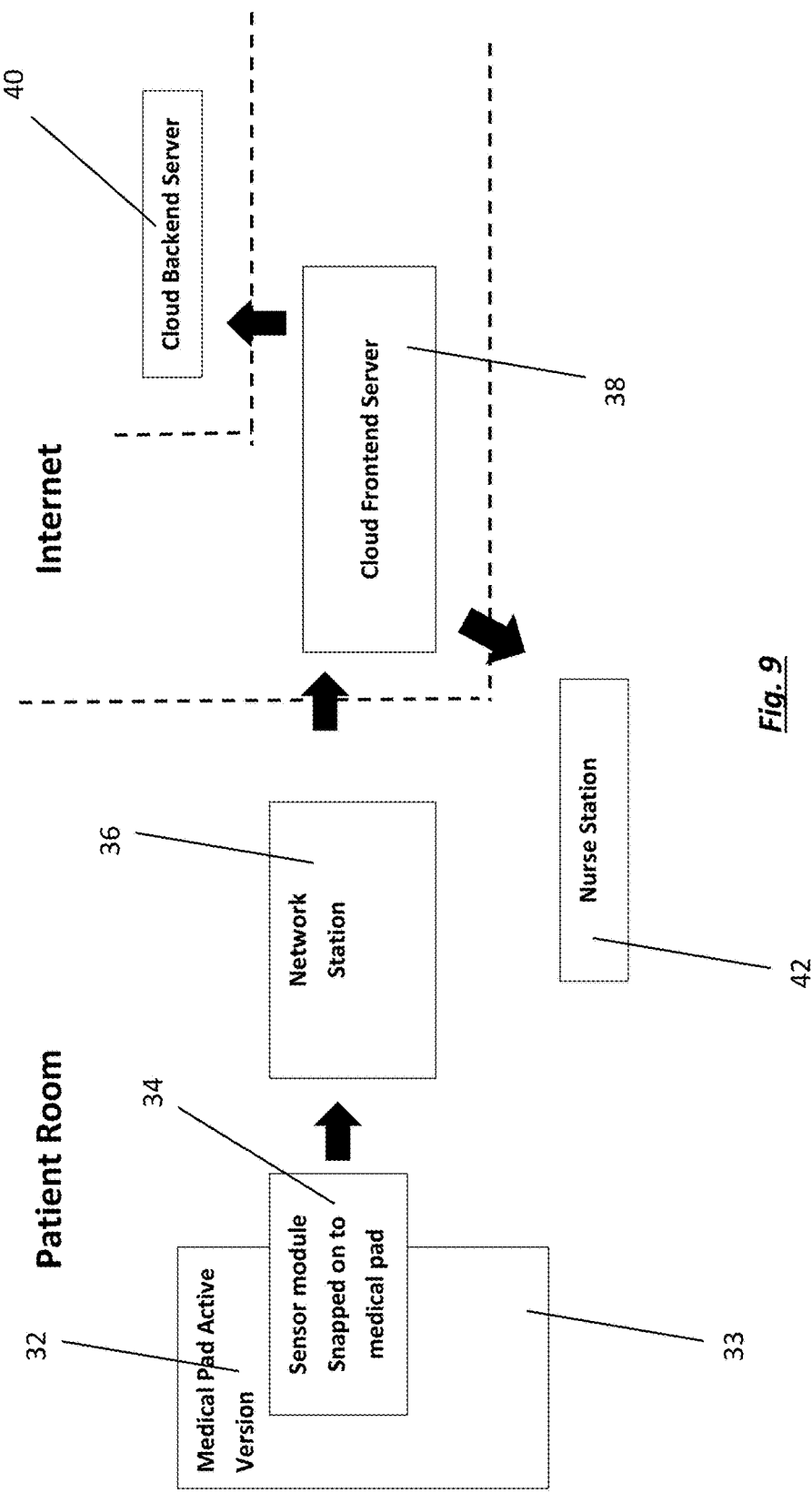
FIG. 9 shows a schematic diagram of an active wetness reporting system according to the present invention.
Figure 10:
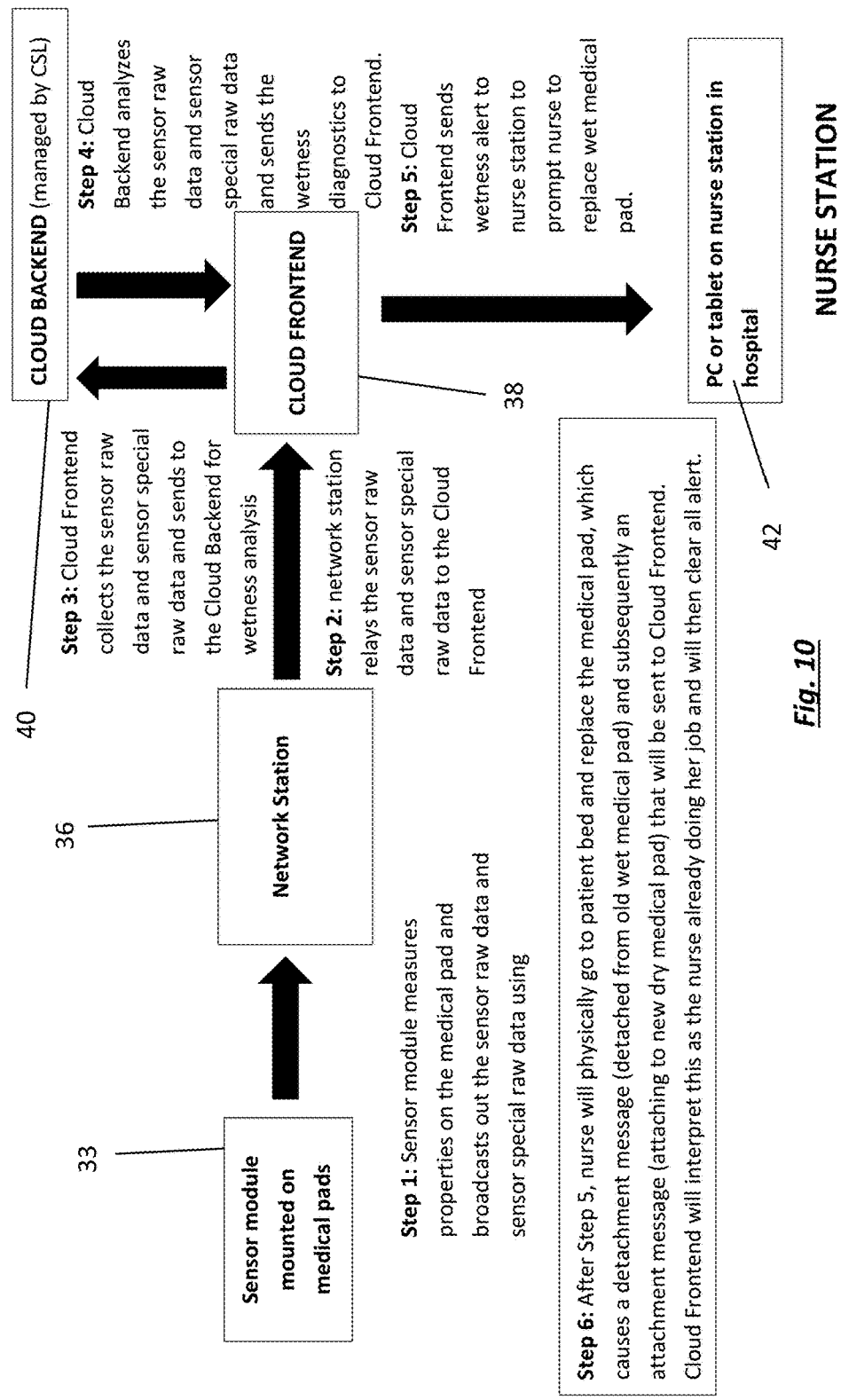
FIG. 10 shows a further schematic diagram of the active wetness reporting system shown in FIG. 9.

Referring to FIGS. 9 and 10, an active wetness reporting system according to an embodiment of the present invention includes the following components:

1. a substrate 32 with a wetness detection circuit;
2. an active sensor module 34 with a wireless data transceiver and a sensor (which may be integrated in an integrated circuit (IC)), which is releasably engageable with (e.g. being snapped on) the substrate 32, reusable, and may be non-rechargeable or rechargeable. The active sensor module 34 and the substrate 32 form an active medical pad 33 according to the present invention.
3. at least one network station 36, which is Ethernet-, Wi-Fi- and Bluetooth-enabled;
4. a Cloud Frontend server 38;
5. a Cloud Backend server 40; and
6. a nurse station 42.

The substrate 32 is contained in the active medical pad 33. The active sensor module 34 is reusable and is attached to the medical pad 33 to measure the electrical properties (including electrical resistance) on the substrate 32 of the medical pad 33 and to broadcast multiple sets of Sensor Raw Data to one or more network stations 36. In particular, the sensor module 34 includes a sensor to sense and measure the electrical resistance of the wetness detection circuit on the substrate 32 of the medical pad 33. The sensor module 34 also sends data indicating its battery voltage to the network station 36 so that a system administrator will know whether the sensor module 34 is nearing the end of its battery life.

The network station 36 (i) takes the broadcasts from the active sensor module 34 and relays the data in the broadcast to the Cloud Frontend server 38, and (ii) handles registration or re-registration of the sensor modules 34 to the Cloud Frontend server 38 for tracking, and allocation to the end user (nurse station 42).

The Cloud Frontend server 38 (i) takes the Sensor Raw Data and Sensor Special Raw Data from the network station 36 and sends such data to a Cloud Backend server 40 for wetness analysis, (ii) takes wetness analysis results from the Cloud Backend server 40 and notifies the nurse station 42 in case a wetness result is obtained, and (iii) takes the battery voltage and determines if it is too low, and alerts the nurse station 42 accordingly, if necessary.

The Cloud Backend server 40 takes the Sensor Raw Data from the Cloud Frontend server 38 and analyzes its wetness level and sends the result back to the Cloud Frontend server 38, for onward transmission to the nurse station 42, to alert the care givers, if necessary. The result may be presented in the form of an indication of "Wet" or "Dry" only. Alternatively, when the analysis indicates wetness of the medical pad 33, an indication of a estimated extent of wetness (possibly represented in percentage) of the medical pad may be provided, e.g. 25% wet.

The nurse station 42 may be a personal computer (PC) or a smart handheld device with LCD screen user interface (user Apps) for nurses, doctors, health care personnel and home care workers who will respond to wetness warning from the Cloud Frontend server 38 and then go to the patient's bed to replace the wet medical pad 33.

Figure 11:
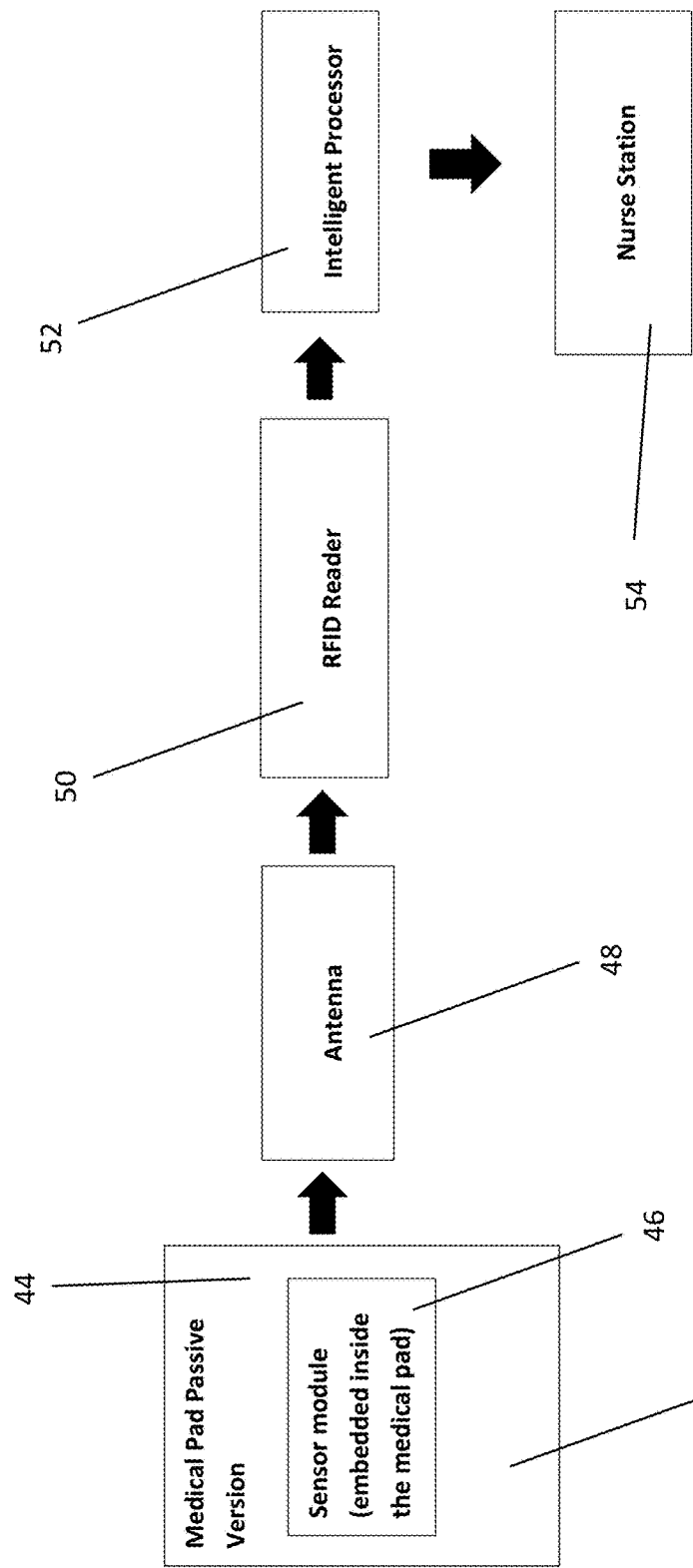
FIG. 11 shows a schematic diagram of a passive wetness reporting system according to the present invention.
Figure 12:
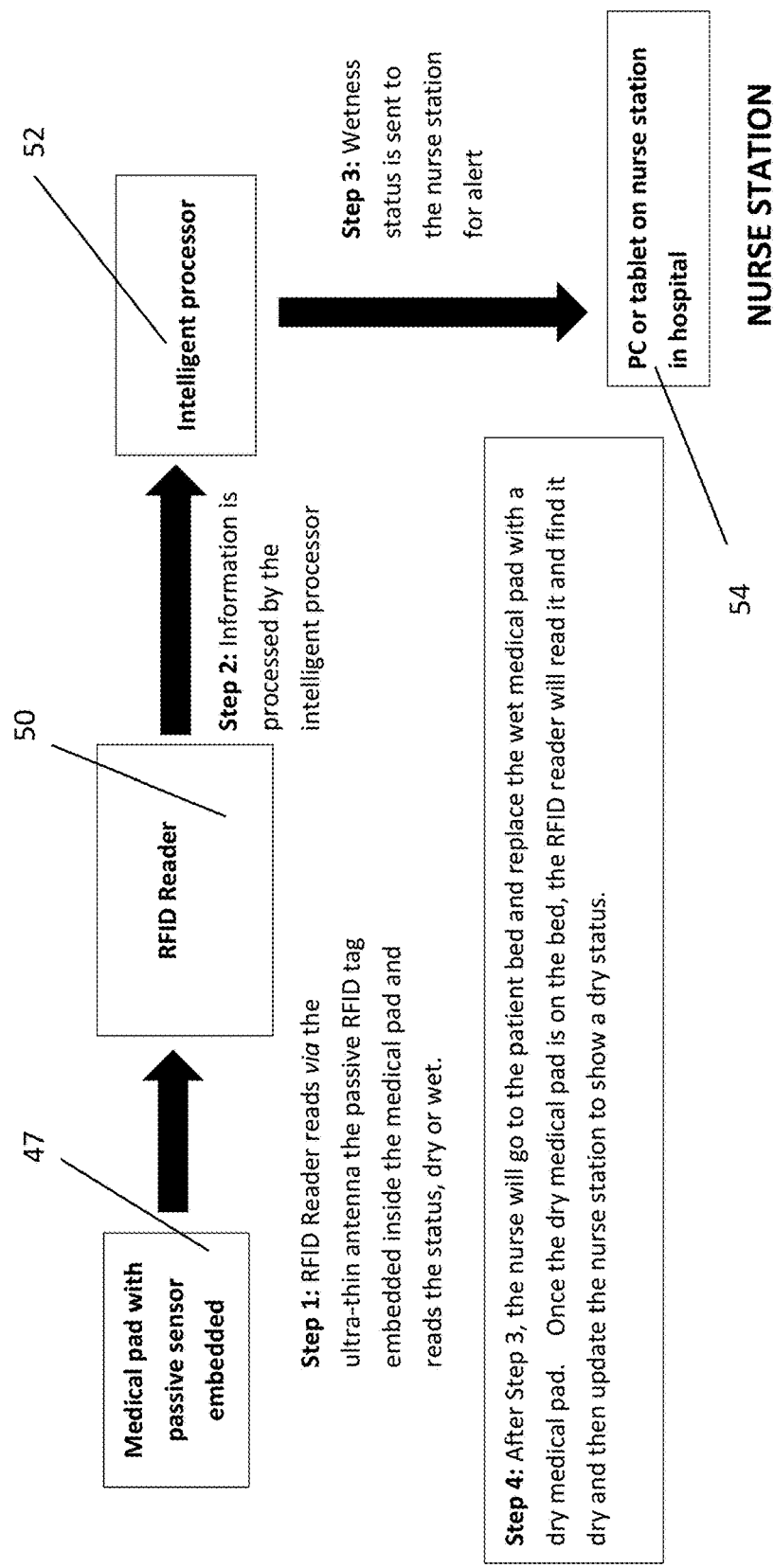
FIG. 12 shows a further schematic diagram of the passive wetness reporting system shown in FIG. 11.

Referring to FIGS. 11 and 12, a passive wetness reporting system according to an embodiment of the present invention includes the following components:
1. a substrate 44 with a wetness detection circuit;
2. a passive sensor module 46 with a passive RFID tag having a matching circuit;
3. an ultra-thin antenna 48 to be positioned underneath a mattress on which the substrate 44 is to be placed;
4. an RFID reader 50 physically connected to the antenna 48 to energize and read data from the RFID tag of the passive sensor module 46;
5. an intelligent processor 52 which controls and reads data from the RFID reader 50, processes the data and decides whether the substrate 44 of the medical pad 47 is wet, and then sends the data, either wirelessly or via Ethernet, to a nurse station 54; and
6. a nurse station 54 which may be a personal computer (PC) or a smart handheld device with LCD screen user interface (user Apps) for nurses, doctors, health care personnel and home care workers who will respond to wetness warning and then go to the patient bed to replace the wet medical pad 47.

The substrate 44 and the passive sensor module 46 are combined and packaged together as a passive wetness reporting medical pad 47 according to the present invention ex-factory.

Figure 13:
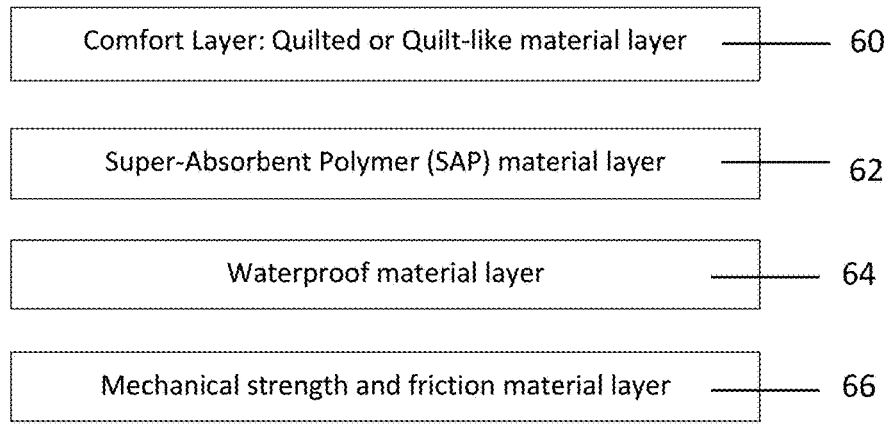
FIG. 13 shows a schematic exploded view of a prior art medical pad.

A conventional general purpose medical pad usually consists of four layers of materials, as shown in FIG. 13:
1. a top comfort layer 60;
2. a water absorption (e.g. Super-Absorbent Polymer) layer 62;
3. a waterproof layer 64; and
4. a mechanical strength and friction layer 66.

Figure 14:
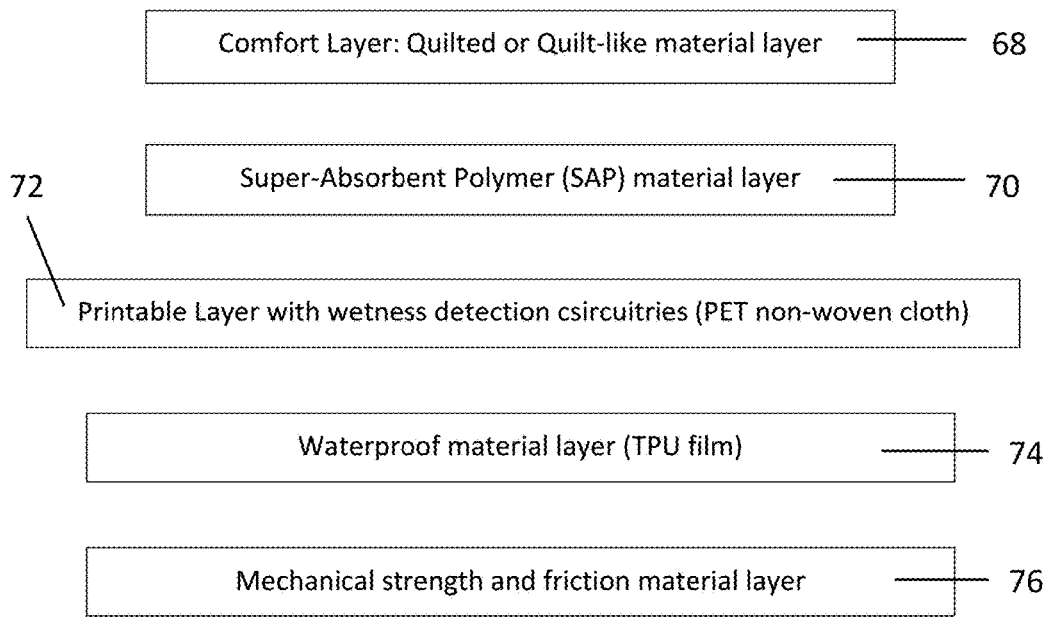
FIG. 14 shows a schematic exploded view of a medical pad according to the present invention.

A medical pad according to the present invention (whether an active medical pad or a passive medical pad) may consist of five layers, as shown in FIG. 14:
1. a top comfort layer 68;
2. a water absorption (e.g. Super-Absorbent Polymer) layer 70;
3. a wetness detection layer (incontinence detection layer), which may be a printable layer (e.g. a piece of polyethylene terephthalate (PET) non-woven cloth) with wetness detection circuitries 72;
4. a waterproof layer (e.g. a thermoplastic polyurethane (TPU) film) 74; and
5. a mechanical strength and friction layer 76.

Figure 15:
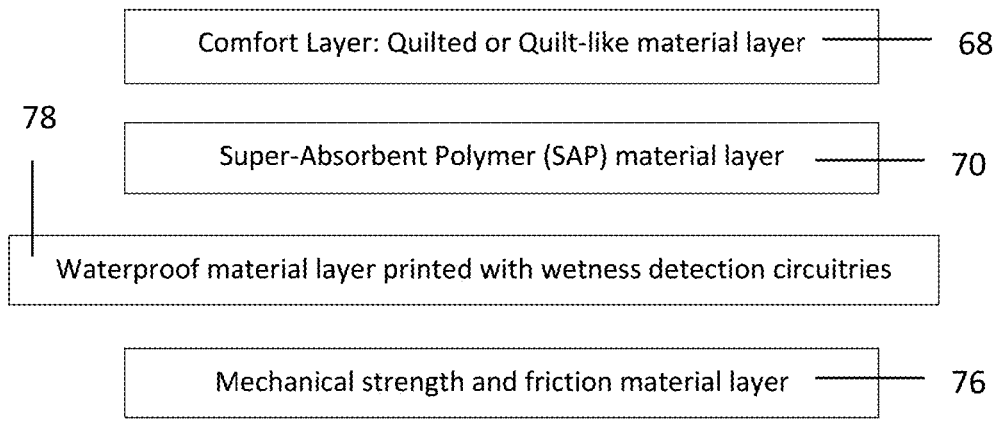
FIG. 15 shows a schematic exploded view of an alternative medical pad according to the present invention.

As shown in FIG. 14, the wetness detection layer 72 may be a separate layer, or, as shown in FIG. 15, may be combined with the waterproof layer 74 to form a combined layer 78, such that the wetness detection circuitries are directly printed on this combined layer 78. This integration becomes a cost down opportunity.

The wetness detection layer 72 and the combined layer 78 contain a wetness detection circuit. The wetness detection circuit consists of electrically conductive lines/traces/wires/threads on the piece of cloth (e.g. a piece of PET non-woven cloth) which are either of a twin wire design or an interlocking comb design. The twin wire design consists of two parallel wires that traverse the piece of cloth in a generally zigzag manner. The terminals entering the twin wires are then tapped, either at one end or both ends. The electrical resistance between the two terminals is then measured.

Figure 16:
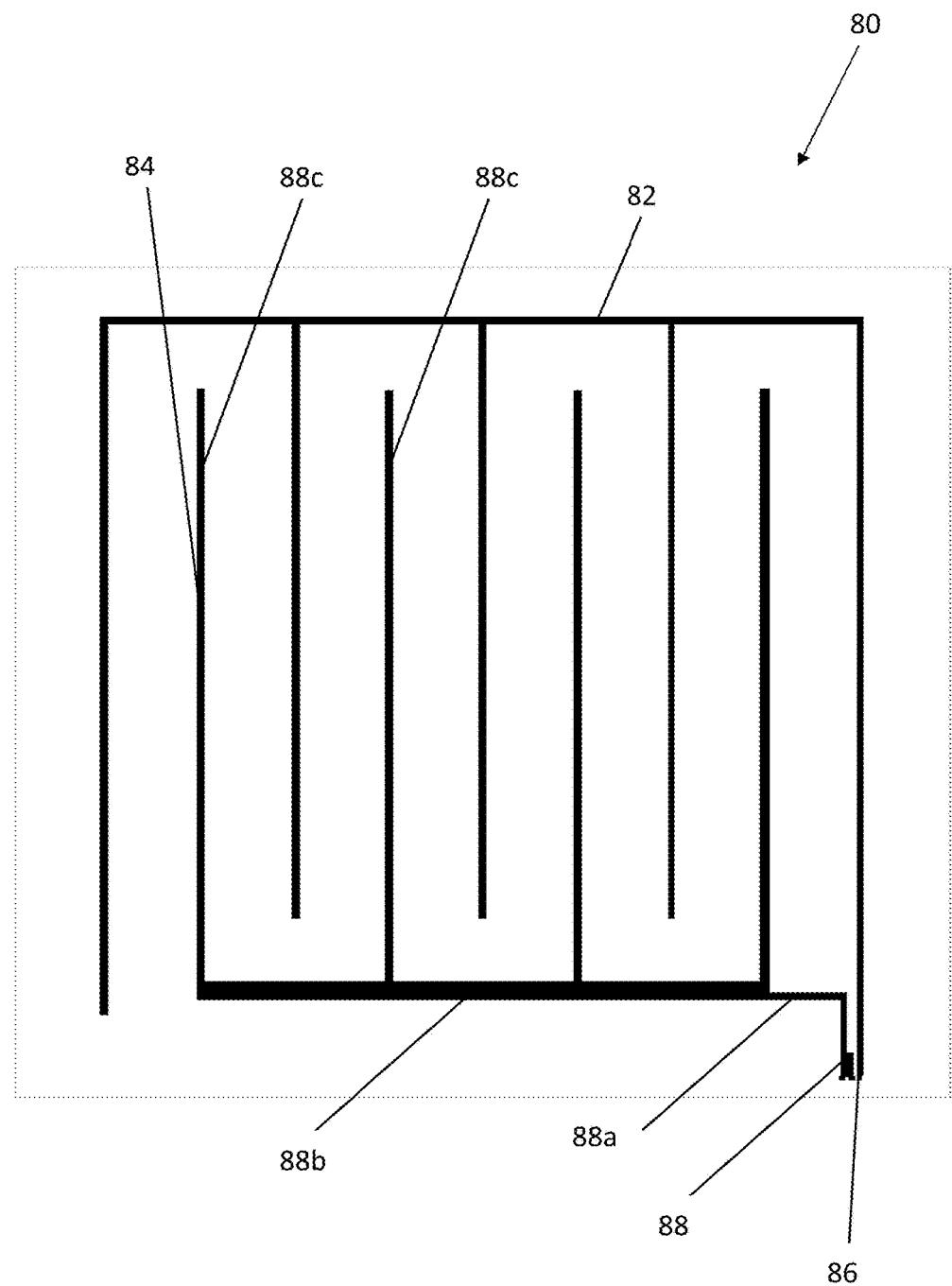
FIG. 16 shows a comb design of a wetness detection arrangement according to the present invention.

The interlocking comb design 80 according to the present invention consists of two conductive lines 82, 84, each forming a comb shape covering essentially the whole cloth, with the two combs facing each other and with their fingers penetrating each other alternately, just like when a human being interlocks his/her fingers, as shown in FIG. 16. Terminals 86, 88 entering these two combs are tapped and the resistance across them is measured. The basic idea of wetness detection is that urine or bowel materials consists of liquid containing chemical ions that are electrically conductive. When this conductive material is spilled on top of the twin wire or the comb circuit, it will short circuit the conductive lines 82, 84. When the detection layer 72 or the combined layer 78 is dry, the electrical resistance between the two terminals 86, 88 is large or infinite. When the detection layer 72 or the combined layer 78 is wet, depending on where and how extensive the wetness is, the electrical resistance between the two terminals 86, 88 will become of different finite values.

The design of the conductive lines 82, 84 of the comb design 80 in the substrate 32, 44 according to the present invention requires a novel method to overcome the fundamental shortcomings of the original design. In the original comb design, all the conductive lines are of the same width. The result is that the section nearest to the entering terminals will be giving false alarms. In addition, the sections further away from the entering terminals will be progressively giving out false alarms. To overcome this, a novel design is introduced such that the conductive line 84 has at least three sections each of a different width, viz. a first section 88*a* leading directly out from the terminal 88 is narrowest, a second section 88*b* leading from the first section 88*a* but before branching out into fingers 88*c* is widest, and finger sections 88*c* branching out from the second section 88*b* are of a width between that of the first section 88*a* and that of the second section 88*b*. Thus, along the conductive line 84, the first section 88*a* is of the highest electrical resistance per unit length, the second section 88*b* is of the lowest electrical resistance per unit length, and the finger sections 88*c* are of an electrical resistance per unit length between that of the first section 88*a* and that of the second section 88*b*. As to the other conductive line 82, such is of a uniform width along its entire length, which is the same as that of the finger sections 88*c* of the conductive line 84. By way of such an arrangement, the novel comb design 80 has a substantially uniform electrical resistance across the whole area.

Figure 17:
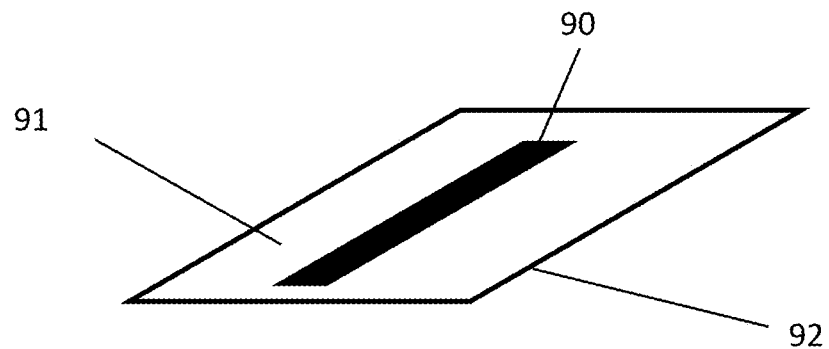
FIG. 17 shows conductive ink printed onto a piece of ink-receptive cloth.
Figure 18:
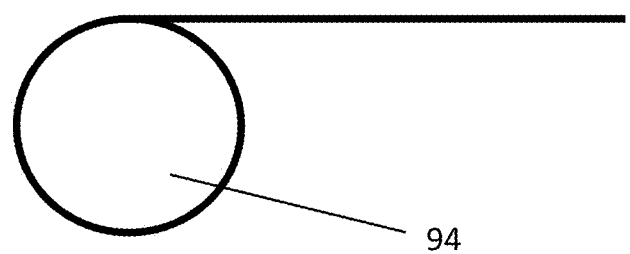
FIG. 18 shows use of roll-printing for printing an electric circuit.
Figure 19:
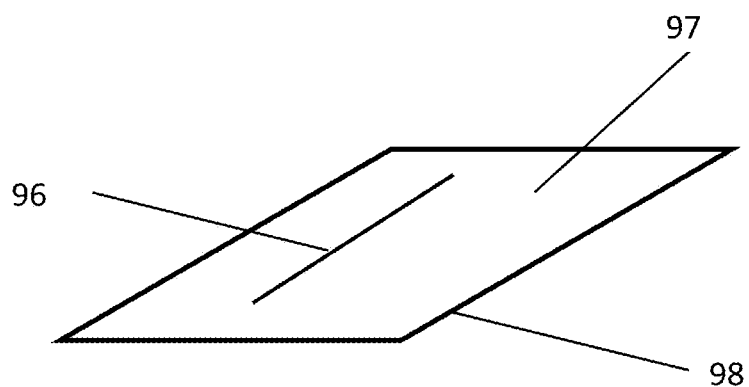
FIG. 19 shows an electrically conductive thread sewn onto a piece of cloth.
Figure 20:
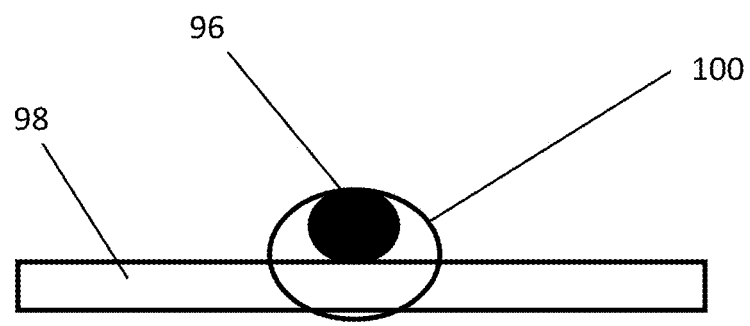
FIG. 20 shows the electrically conductive thread of FIG. 19 covered by yarn.

As explained above, the wetness detection circuit on the piece of cloth provided with the wetness detection circuit consists of conductive lines 82, 84. The conductive lines 82, 84 on the piece of cloth can be fabricated by printing conductive ink (as shown in FIGS. 17 and 18) or by sewing metallic lines on the piece of cloth, as shown in FIGS. 19 and 20. In the printing method, and as shown in FIG. 17, electrically conductive ink 90 is printed onto a major surface 91 of a special ink-receptive cloth 92 by roll printing, as shown in FIG. 18, in which a drum stencil 94 is used for defining the wetness circuitries. In the sewing method, and as shown in FIG. 19, electrically conductive threads 96 are sewn onto a major surface of a piece of cloth 98 using a multi-head sewing machine. As shown in FIG. 20, the conductive threads 96 are on top of the piece of cloth 98, with normal yarn 100 sewn over and below the piece of cloth 98, hence surrounding and buffeting the conductive threads 96.

Figure 21:
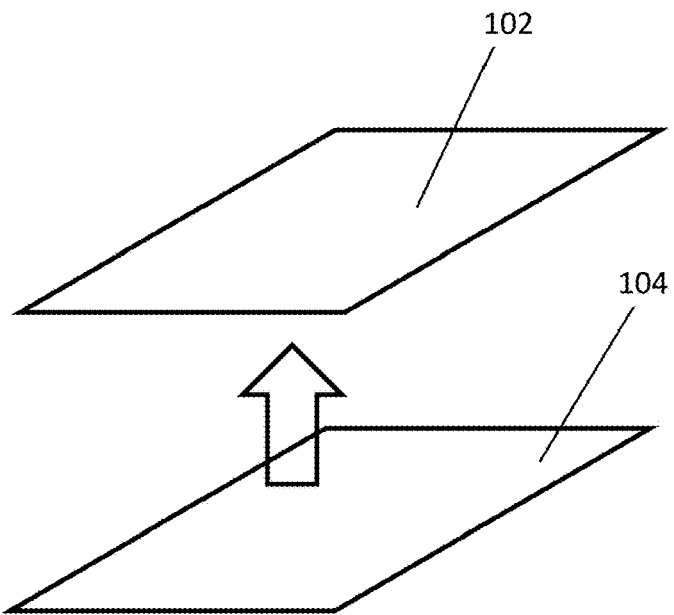
FIG. 21 shows a double pre-laminated layer in the medical pad according to the present invention.
Figure 22:
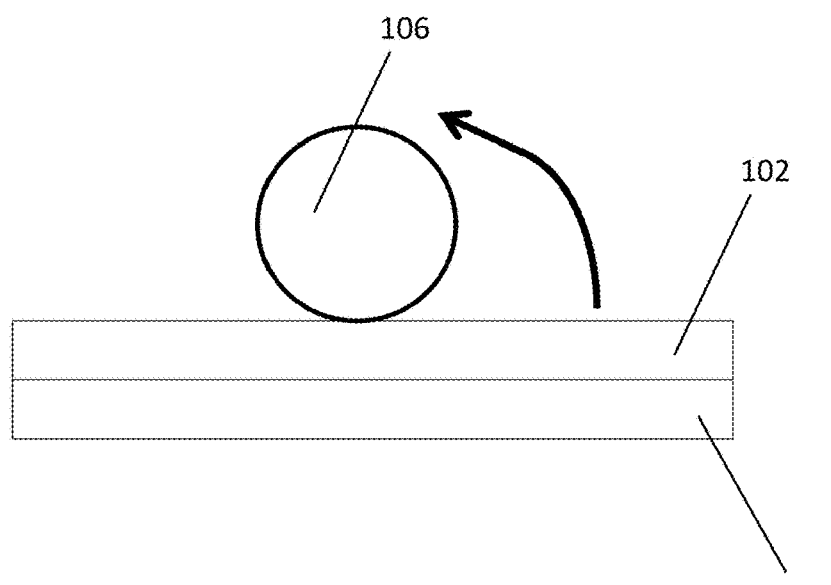
FIG. 22 shows a patient lying on a medical pad with the double pre-laminated layer shown in FIG. 21.
Figure 23:
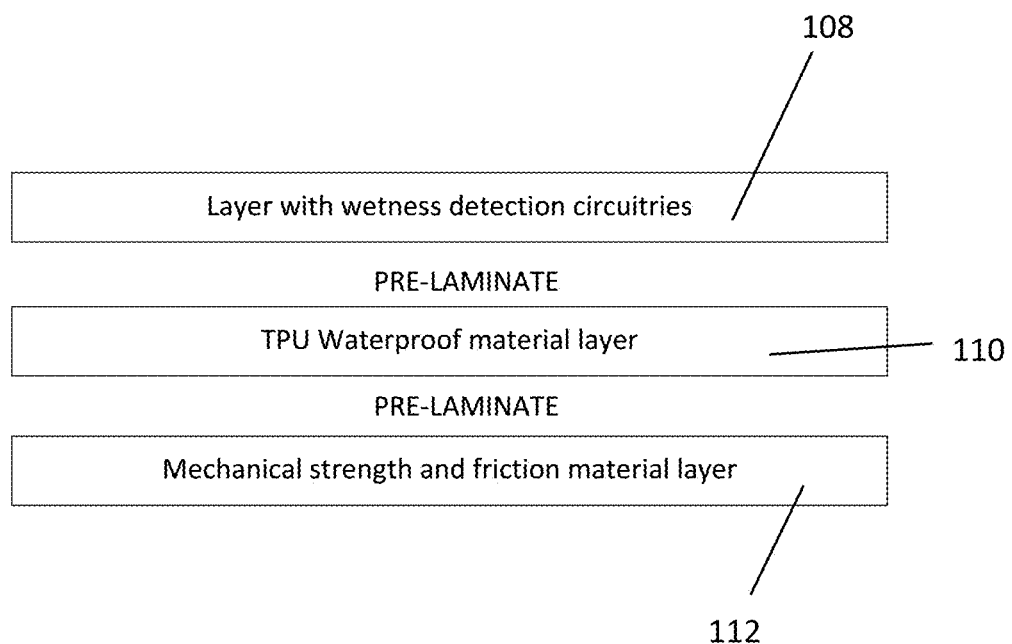
FIG. 23 shows a triple pre-laminated layer in the medical pad according to the present invention.

Choice of the material for the wetness reporting medical pad according to the present invention is complicated because the conductive ink printing process requires roll printing and enclosed environment machine curing. A novel method is here employed where, as shown in FIG. 21, a printable layer 102 and an underlying waterproof layer 104 are pre-laminated with each other to give special strength to significantly reduce shrinkage and deformation of the layer during the curing process. For example, the printable layer 102 may comprise a piece of polyethylene terephthalate (PET) non-woven cloth, and the waterproof layer 104 may comprise a thermoplastic polyurethane (TPU) plastic film 104, to give extra high temperature resistance in the ink curing process, extra high tensile strength, tear strength and puncture strength, when they are laminated with each other. The overall tensile strength of the medical pad is extremely important because it is now becoming a common practice for nurses to use the medical pad as a means to assist in rolling over of the patient 106—i.e. the periodic rolling requirement to reduce the chance of occurrence of bed sores, as shown in FIG. 22. If the medical pad is not strong enough, it would be torn apart by the nurse during this roll over action. Even if it is not torn apart, the stretching of the detection layer with the wetness detection circuit will cause the electrical resistance of the circuit to increase so much that the measurement is no longer valid. To overcome these multiple issues, and as shown in FIG. 23, a medical pad according to the present invention includes, in addition to a top SAP layer (which is not shown in FIG. 23), a triple-laminated structure consisting of a piece of polyethylene terephthalate (PET) non-woven cloth 108 provided with a wetness detection circuit, a layer of waterproof high temperature thermoplastic polyurethane (TPU) plastic film 110, and a mechanical strength and friction material layer 112 (which may be a piece of polypropylene (PP) non-woven cloth), all pre-laminated with one another, and with the piece of TPU plastic film 110 sandwiched between the piece of PET non-woven cloth 108 and the piece of PP non-woven cloth 112. When assembled, the piece of PET non-woven cloth 108 is next to and in contact with the SAP layer.

As an alternative, the TPU film may be replaced by a TPU based, or polyamide (PA) based (such as nylon based), or propylene oxide (PO) based, or ethylene-vinyl acetate (EVA) based, or thermoplastic rubber (TPR) based, or PET based, but not limited to the above, hot melt adhesive structure (which is a waterproof structure), with a special application and curing process. This hot melt adhesive structure will provide both the strengthening process for the printable cloth curing process, and waterproof function.

With all these special methods, the wetness detection medical pad design is optimized, but as of all manufacturing, there will still be tolerance and variation in the material, including the ink resistivity, etc. Calibration, more particularly continuous calibration, or real time self-calibration, of the wetness detection circuit on the medical pad 33 is needed to handle the variation of electrical resistance of the conductive lines in the wetness detection circuit in the medical pad 33 due to:

(a) variation in production between lots;
(b) variation in the environmental humidity,
(c) action by the nurse to roll over the patient by using the medical pad 33 as a lift-helping tool,
(d) action by the nurse to shift the patient by using the medical pad 33 as a shift-helping tool, and
(e) action by the nurse to lift up the patient by using the medical pad 33 as a lift-helping tool.

By adapting to the changing environment and changing material properties as described above, the system is able to give a correct result.

Figure 24:
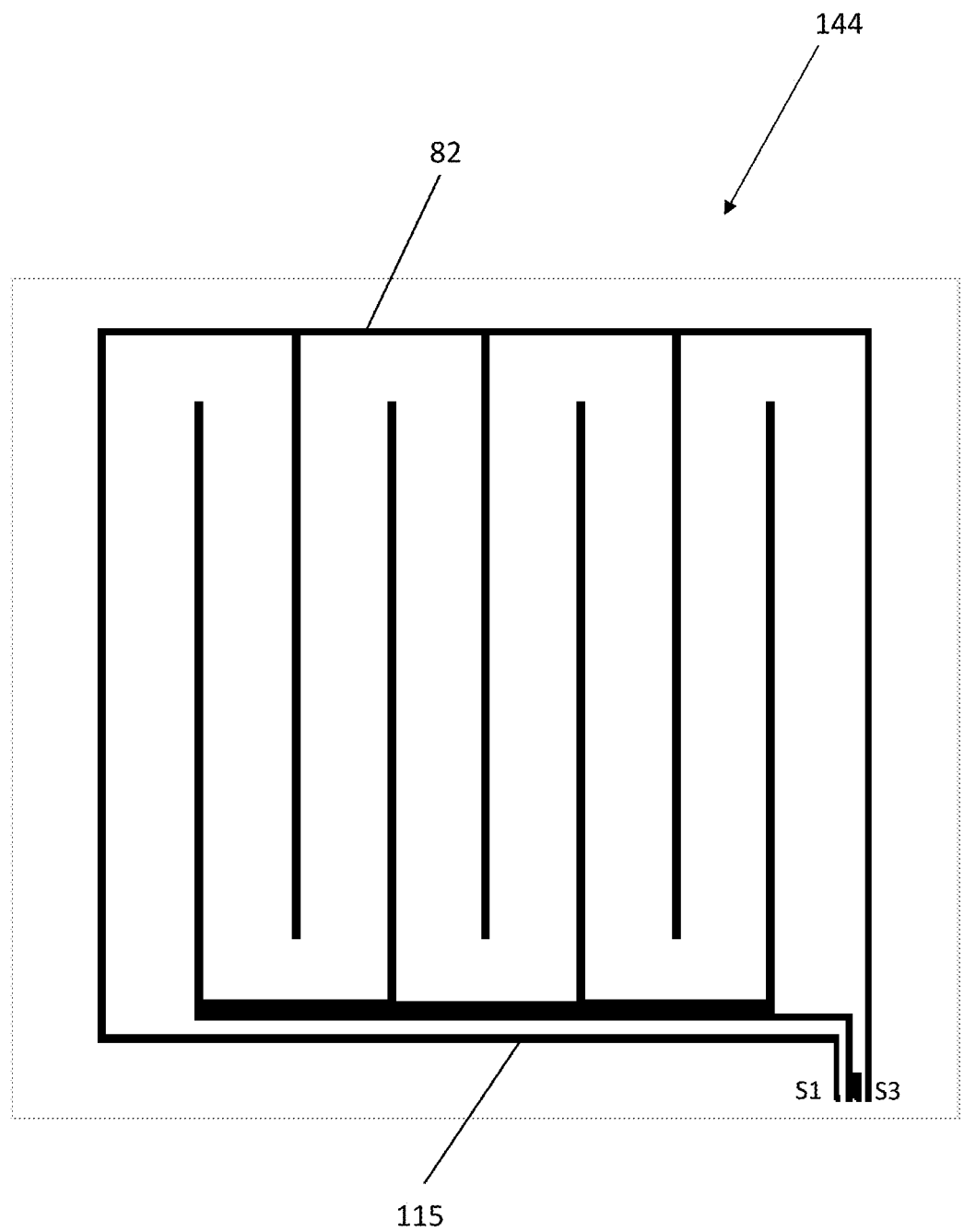
FIG. 24 shows the comb design of the wetness detection arrangement of FIG. 16, further improved for allowing calibration.

To achieve this real time self-calibration, and as shown in FIG. 24, a novel way is introduced to measure the electrical resistance between terminal S1 and S3 to calibrate the medical pad wetness detection circuit 114. S1 is a further terminal connected with the conductive line 82 via a calibration conductive line 115, forming a closed loop. The electrical resistance of the calibration conductive line 115 is measured and uploaded to the Cloud Frontend server 38 and then sent to the Cloud Backend server 40 when the sensor module 34 is attached to the medical pad 33. This calibration line electrical resistance value is used in the final calculation of the wetness. Lot by lot records of the range of calibration values are stored in the Cloud Backend server 40 for further characterization of the medical pads 33. Correlation of the medical pads 33 with the specific lots are also used for improving the accuracy of the measurement.

In addition, the sensor in the active sensor module 34 continues to regularly carry out real-time self-calibration on the medical pad wetness detection circuit 114 of the medical pad 33, by measuring the electrical resistance value of the calibration conductive line 115, so long as the active sensor module 34 is attached to the medical pad 33, every time the transmitter in the active sensor module 34 broadcasts a Keep Alive beacon (which indicates that the active sensor module 34 is alive and operating), e.g. every ten minutes, and every time the active sensor module 34 is attached to a medical pad 33. For the first-time calibration of the wetness detection circuit 114 of the medical pad 33, the actual measured value of the electrical resistance of the calibration conductive line 115 is obtained, transmitted to the Cloud Frontend server 38, and then transmitted and stored in the Cloud Backend server 40. For subsequent calibration, only the difference between the newly measured value and the first-time measured value is transmitted to the Cloud Frontend server 38, and then transmitted and stored in the Cloud Backend server 40. The measured calibration value of the electrical resistance of the calibration conductive line 115 is used for determining if the medical pad 33 is wet, and, if so, the estimated extent of wetness, as expressed in percentage. This adaptive real time self-calibration method allows the system to actively monitor the conditions of the medical pad 33 and to give correct wetness diagnosis even in the face of changing environment and changing material properties.

Figure 25:
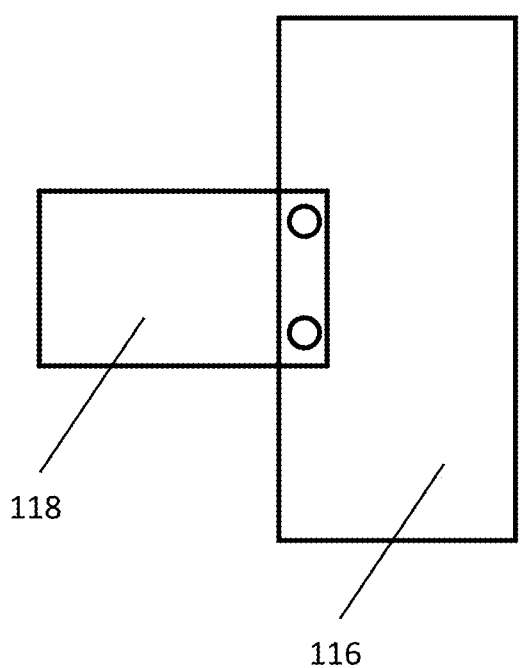
FIG. 25 shows a passive sensor module according to the present invention.

As shown in FIG. 25, a passive sensor module 46 for a passive wetness reporting medical pad system consists of a passive RFID tag 116 connected to a matching circuit 118 (on a flexible printed circuit board (PCB)) consisting of a series and/or parallel resistor, capacitor and inductor circuit, in particular a matching π-circuit (pi-circuit). The RFID tag 116 consists of an RFID IC in die form, glued to a loop matching circuit and then a dipole antenna consisting of various shapes and designs.

Figure 28:
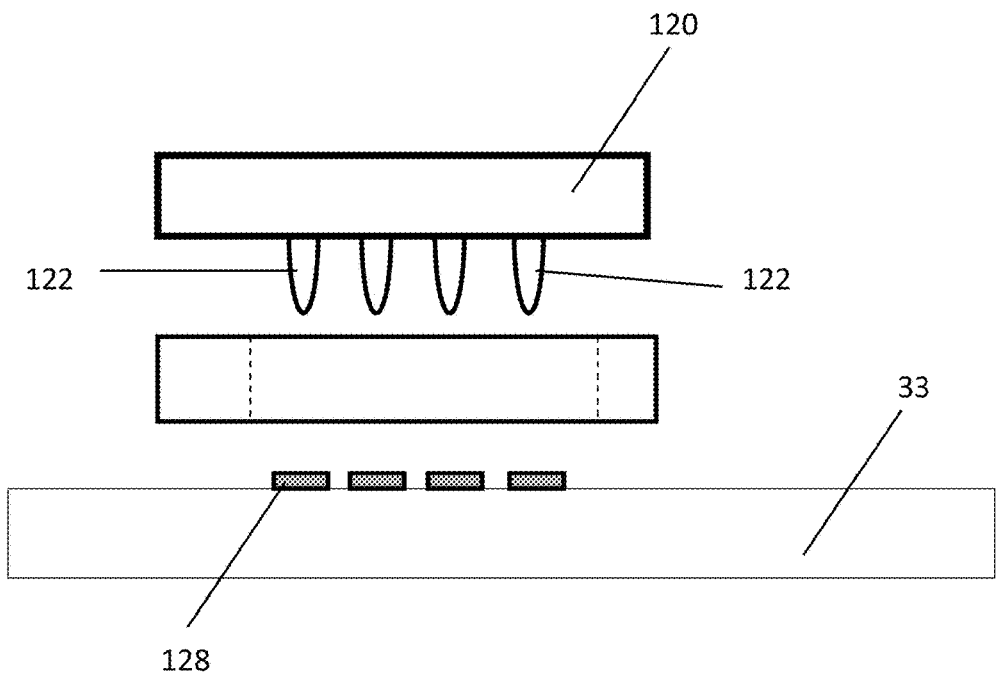
FIG. 28 shows electrical connection between the active sensor module of FIG. 26 with the medical pad according to the present invention.
Figure 29:
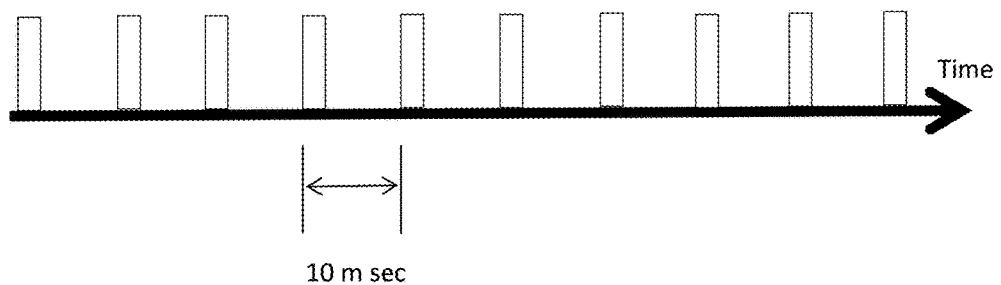
FIG. 29 shows pulsed measurement of the wetness detection circuit on the medical pad according to the present invention.
Figure 30:
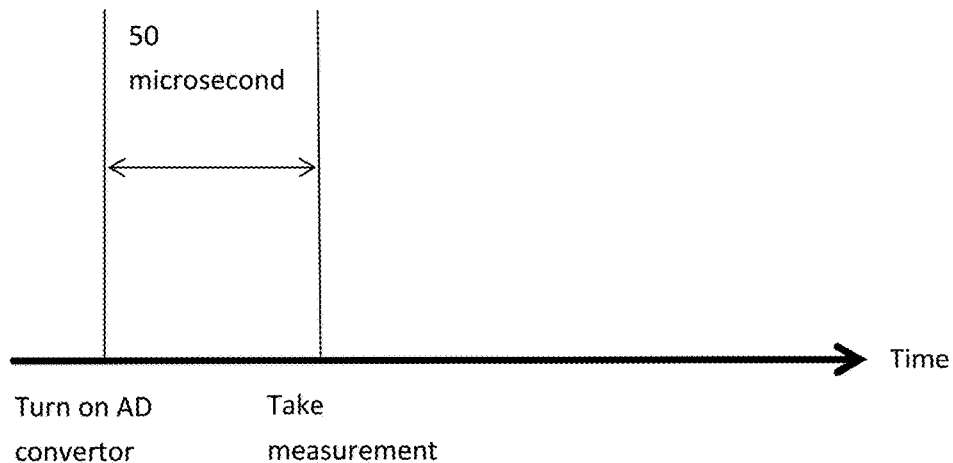
FIG. 30 shows delayed measurement of the wetness detection circuit on the medical pad according to the present invention.

As for active sensor modules 34 for active incontinence detecting medical pad system, and as shown in FIGS. 26 and 28, such consist of a snapped-on, by magnetic force, sensor unit 120 with multiple waterproof spring-loaded pogo pins 122 that will press onto the medical pad 33, connecting with the wetness detection circuit 128 on the detection layer. As shown in FIG. 27, a docking 124 on the medical pad 33 with a piece of ferromagnetic metal 126 in the center is designed to mate with a piece of magnet in the sensor unit 120. Once the active sensor module 34 is attached to the medical pad 33, and after an initial time delay, the active sensor module 34 starts to sense and measure the electrical resistance of the wetness detection circuit by measuring the electrical resistance between various pairs of the pogo pins 122. The measurement is done in a pulsed manner (see FIG. 29), e.g. 10 times 10 ms cycle measurement, each measurement taking 150 microsecond (0.15 ms). The result is then averaged. Such an arrangement can avoid electrically modifying the electrical properties of the spilled urine or bowel material. The measurement is also done with careful time delay, as shown in FIG. 30. For example, the measurement is set to be taken only after 50 microsecond after turning on the DC power supply. Both of these methods are used for correcting measurement for prolonged period of time. The ultimate goal is to give a correct warning notification when the medical pad is wet.

Figure 31:
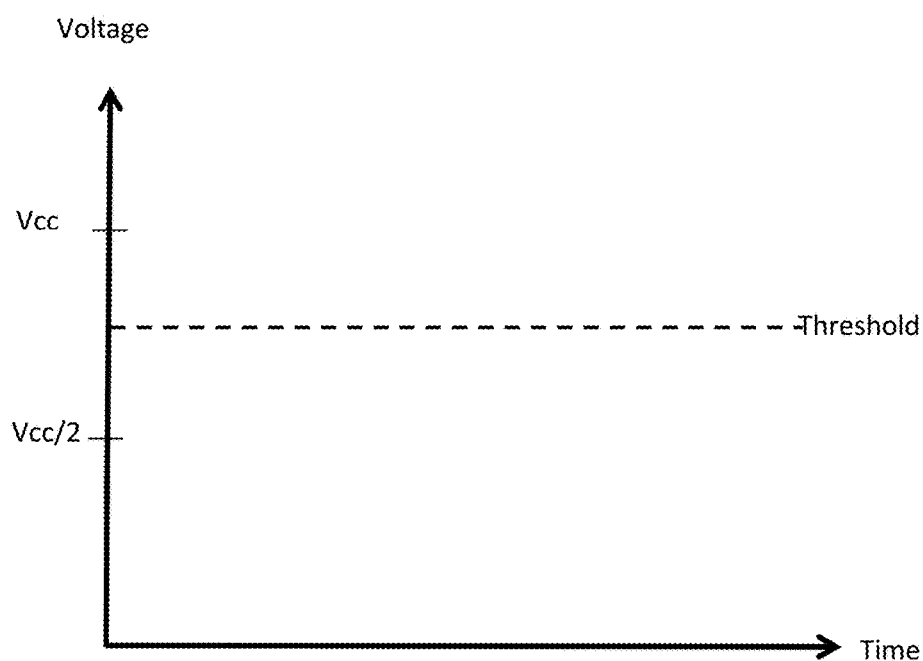
FIG. 31 shows determination of clogging of pogo pins of the active sensor module according to the present invention.

In operation, due to urine and bowel material spilled onto the medical pad 33, it is possible that the pogo pins 122 of the sensor unit 120 get clogged and the spring action be stymied. To detect this situation, a novel method is introduced to detect whether a pin 122 is clogged at the point of attachment. As shown in FIG. 31, if a certain pin 122 is clogged, the measured voltage at the pin 122 as measured by the senor in the IC is near to Vcc inside. If not clogged, then the measured voltage as measured by the sensor is 0.5 Vcc. One can therefore set a voltage threshold to differentiate between these two voltage levels. If clogging happens and is detected by the sensor in the IC, a clogged beacon is sent out to the Cloud Frontend server 38, which will then send a notification to the nurse station 42. Also, an LED light on the sensor module 34 will not light up. The nurse, when seeing the absence of the LED light turning on, will realize that either the sensor module 34 is clogged or the battery is used up. The nurse can then verify which one is true by checking with the nurse station 42 (a personal computer, iPAD®, or Android® Pad).

Figure 32:
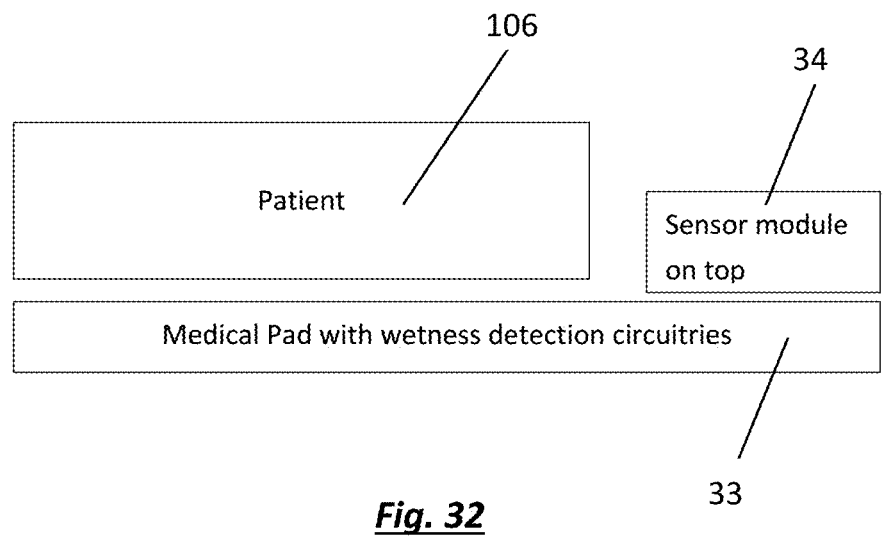
FIG. 32 shows positioning of the active sensor module on the medical pad according to the present invention.
Figure 33:
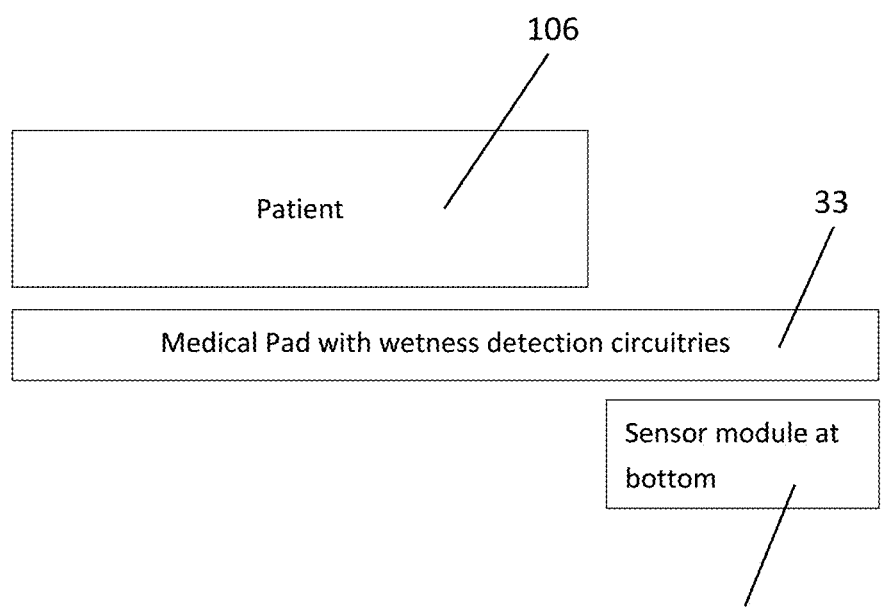
FIG. 33 shows positioning of the active sensor module under the medical pad according to the present invention.
Figure 34:
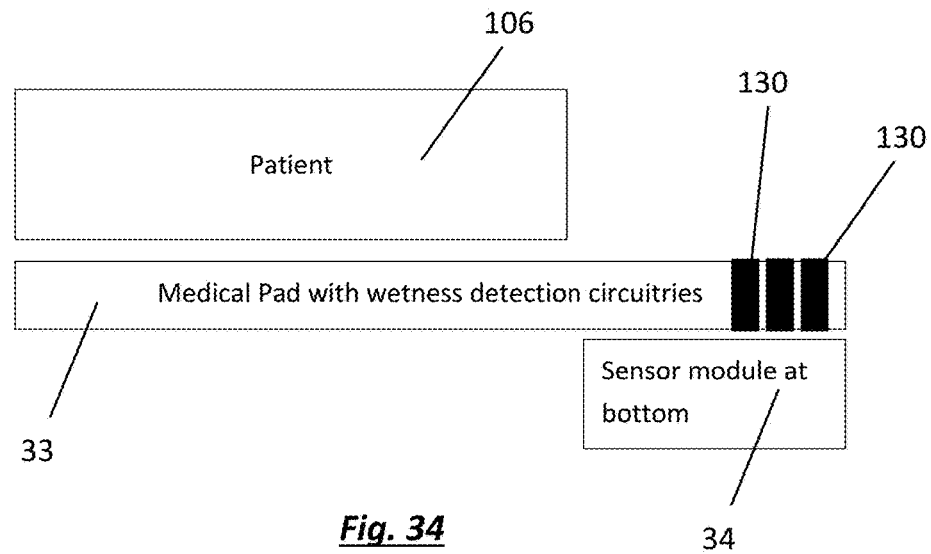
FIG. 34 shows connection of the active sensor module to the medical pad according to the present invention.

For the active sensor module 34, it can be snapped on the top of the medical pad 33, i.e. the side nearer to the patient 106 (as shown in FIG. 32), or, as shown in FIG. 33, on the bottom of the medical pad 33, i.e. the side facing the mattress. Snapping on the top is easier for the nurse to mount. Snapping on the bottom has the advantage that the patient 106 cannot easily play with it, move it out of the snapping dock or contact the patient's skin. It depends on the actual environment and patient condition to decide which arrangement is more suitable. In case of snapping the sensor module 34 on the bottom, and as shown in FIG. 34, metal eyelets 130 are mounted on the end of the trace so that the sensor pogo pins 122 can connect from the bottom to the top circuitry.

Figure 35:
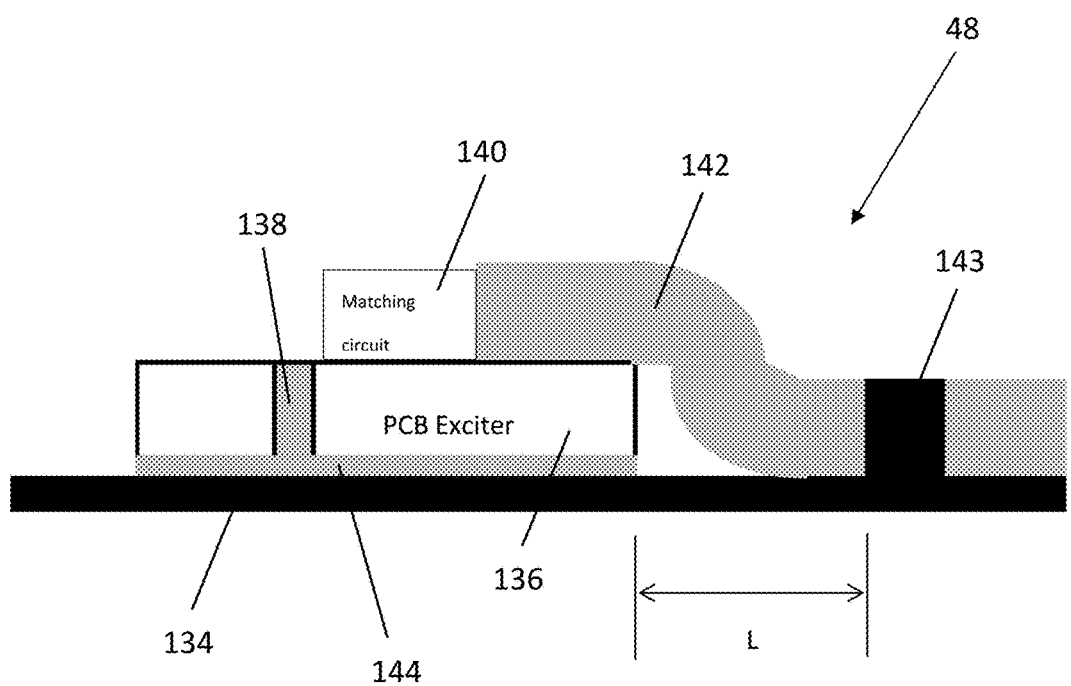
FIG. 35 shows a sideway excitation arrangement used in a passive incontinence detecting medical pad according to the present invention.

The passive wetness reporting solution uses RFID readers 50 and antennae 48 to illuminate the RFID tag based sensor module 46, energizing it and then reading out the wetness measurement. The antenna 48 used in this system is the CS790 series ultra-thin antenna of Convergence Systems Limited. This antenna 48 is designed based on the original design disclosed in US Patent Application Publication No. US 2012/0249395 A1, but modified to become a cased antenna with RF cable entering from the side. This is done using a novel sideway excitation circuit with a special way of shorting the outer surface of the cable entering the unit, as shown in FIG. 35. The antenna 48 has a back metal ground 134 mounted with a PCB exciter 136 having a via hole 138. A matching circuit 140 connects the centre pin of a coaxial cable 142 to the via hole 138. The coaxial cable 142 is short to the metal ground 134 by an external connector 143 at a distance L away from the PCB exciter 136. A tape 144 is positioned between the PCB exciter 136 and the back metal ground 134 to isolate the via hole 138 from the ground 134. As shown in FIG. 36, this novel modified antenna 48 is further hermetically sealed to allow medical sterilization, which is unsuitable on the original design.

This antenna 48 operates with a novel leaky wave travelling wave mechanism, with the wave leaking out from the top surface of a parallel plate travelling wave waveguide, with this top surface in a crossed mesh of conductive aluminum material. Basically the wave leaks out from the slots of the crossed mesh and its energy drops exponentially. With this novel mechanism, the energy leaving the ultra-thin antenna 48 forms a limited detection zone above the mattress, just covering that area and not cross reading the medical pad on a nearby bed. This is very important because, with adjacent beds with patients of different needs, as shown in FIG. 37, if the RFID reader 50 erroneously reads the RFID tag of a medical pad 47 from an adjacent bed, the nurse may be rolling over the wrong patient. This novel antenna 48, with its ultra-thin nature (hence can be mounted right under the mattress) and leaky wave travelling wave nature (hence the energy can be well contained within the top of the mattress), is an important technology enabler of this passive incontinence system.

Figure 38:
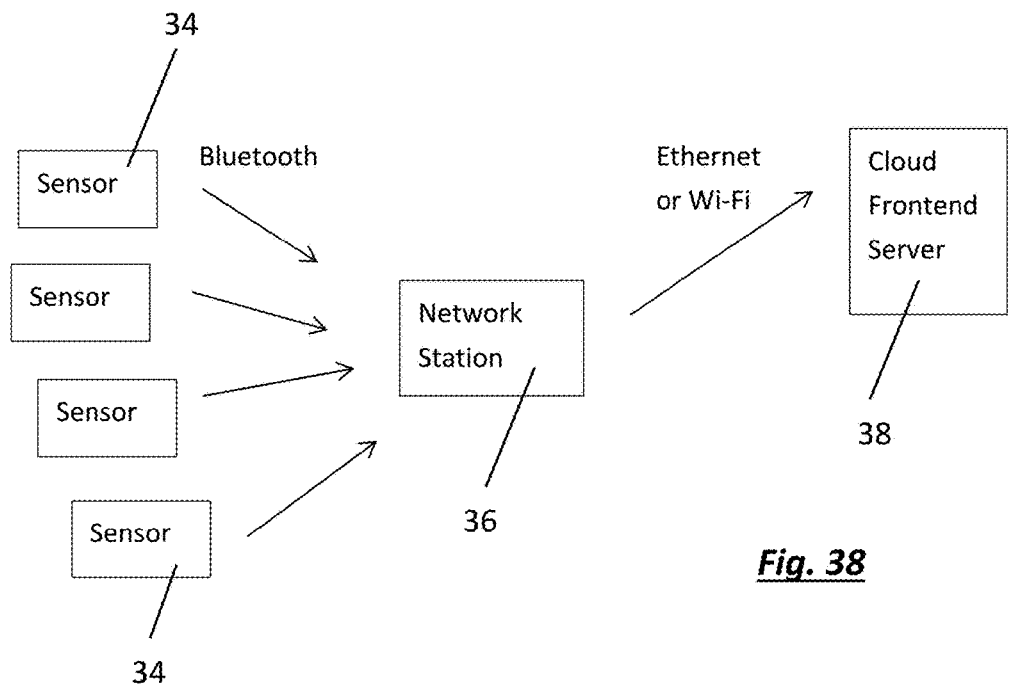
FIG. 38 shows a configuration of a wetness reporting system according to the present invention.

As shown in FIG. 38 of the active wetness reporting system according to the present invention, the network station 36 performs the following functions:
a) bridges (relays) the Bluetooth® broadcast from the sensor modules 34 to the Cloud Frontend server 38, either through Ethernet or Wi-Fi technology, and
b) provides a cradle for the sensor modules 34 to do registration (or re-registration) to the Cloud Frontend server 38, which also allows the nurse to map the patient name to the respective sensor module 34.

The active wetness reporting system according to the present invention consists of the sensor modules 34 broadcasting their respective wetness measurement data via Bluetooth® Low Energy protocol based beacon and collected by the bridge network station 36. This network station 36 relays the information via the Internet to the Cloud Frontend server 38. The network station 36 takes in the Bluetooth® Low Energy beacon, adds its own identification information, encrypts further and sends to the Cloud Frontend server 38.

Figure 39:
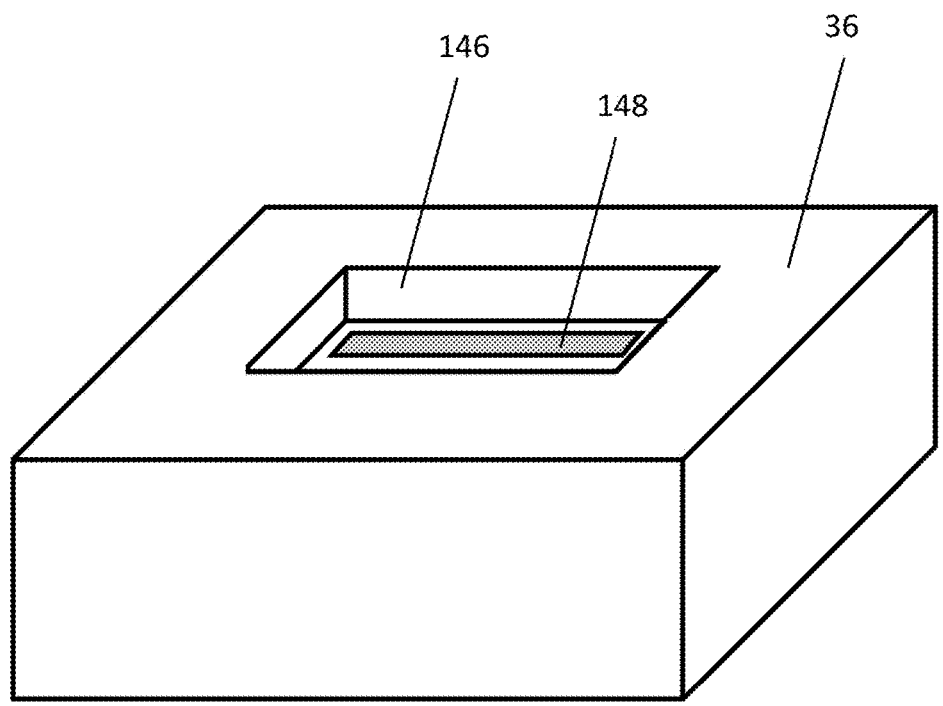
FIG. 39 shows a schematic drawing of a cradle in a nurse station of the wetness reporting system shown in FIG. 38.

As shown in FIG. 39, the network station 36 also contains a cradle 146 that allows the nurse to put the sensor module 34 on it. This will allow the network station 36 to perform a registration or re-registration function. The registration function is carried out whenever the nurse takes a new and fresh sensor module 34 and wants to register the sensor module 34 to the system and associate it with a new patient. The re-registration function is carried out when an old sensor module 34 has been cleaned up and a nurse wants to register it to the system and associate it with another patient. A metal plate 148 in the cradle 146 will short all the pogo pins 122 of the sensor module 34 to signal to the sensor module 34 that it is to undergo a registration (or re-registration) process. When an old (and used) sensor module 34 is placed in the cradle 146, all information relating to the previous patient as stored in the sensor module 34 will be erased, for re-registration purposes.

If there are multiple registration cradles 146 nearby, the start up registration request beacon will be "heard" by all of them. They would not know which particular registration cradle 146 the sensor module 34 is actually on. A novel way is used for determining whether the sensor module 34 is attached to the desired registration cradle 146, in which the absolute received signal strength indication (RSSI) of the sensor module 34 as read by that registration cradle 146 is measured and a threshold value of 190 is used. If the RSSI of the sensor module 34 as received and measured by a certain registration cradle 146 is above 190 RSSI, then that sensor module 34 is deduced to be actually on the registration cradle 146.

Figure 40:
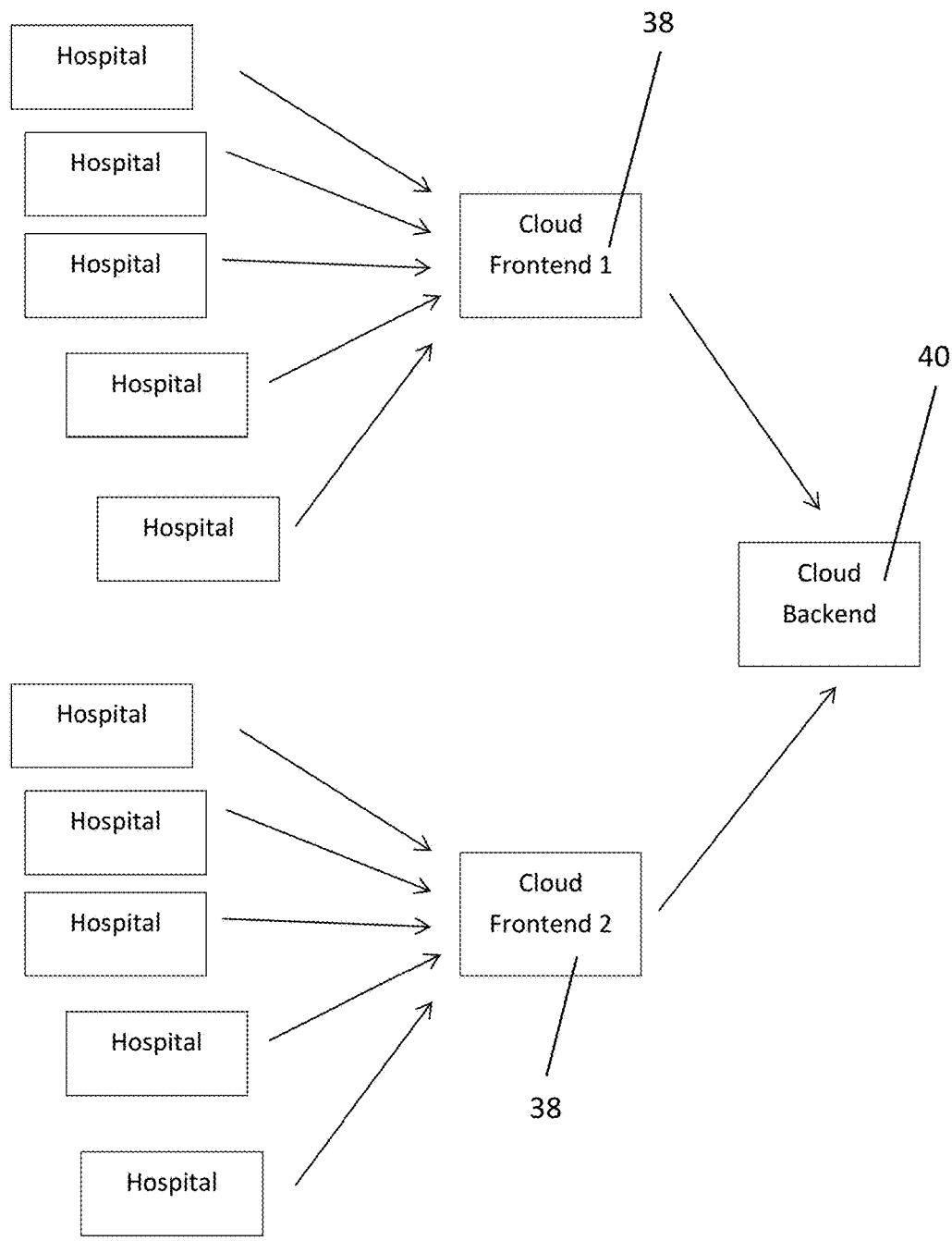
FIG. 40 shows a further configuration of a wetness reporting system according to the present invention.

The Cloud Frontend servers 38 are the interface to all the network stations 36 deployed by a particular service provider of the active wetness reporting system according to the present invention. This Cloud Frontend servers 38 are deployed by medical wetness reporting service providers, each of them providing service to a certain market segment, such as hospital, skilled nursing facilities, home care services, etc. These service providers may be serving a certain geographical segment, such as California only, or serving a certain type, such as Veterans hospital only, etc. In summary, and as shown in FIG. 40, there will be many instances of Cloud Frontend servers 38 deployed in the Internet.

Figure 41:
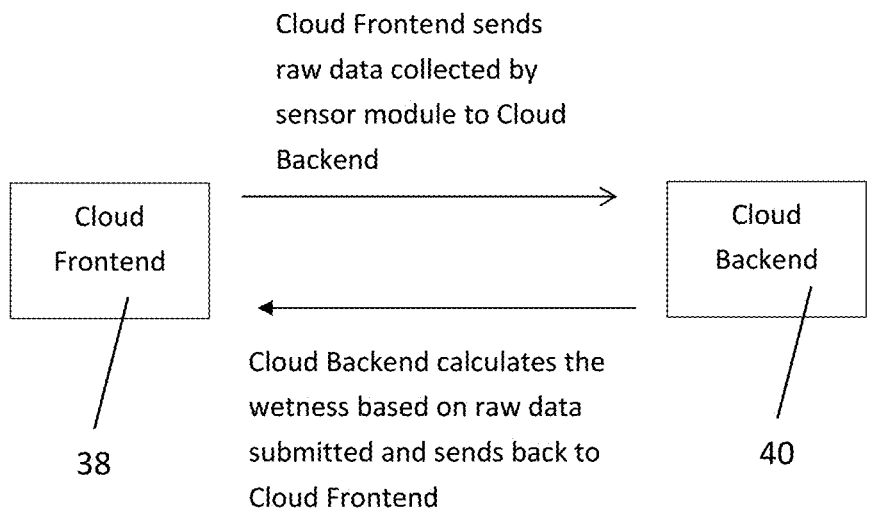
FIG. 41 shows schematically the connection between the Cloud Frontend server and Cloud Backend server of the wetness reporting system according to the present invention.

As shown in FIG. 41, the Cloud Backend server 40 provides the final wetness calculation service and returns the wetness information back to the Cloud Frontend servers 38.

For normal wetness information operation, the Bluetooth® Low Energy beacon is used for sending data out from the sensor modules 34. In fact, the sensor modules 34 send out beacons of various contents:

1. Keep Alive beacon, indicating that the sensor module 34 is active;
2. Wet Status beacon, indicating that the medical pad 33 is wet;
3. Attachment beacon, indicating that the sensor module 34 has been attached to the medical pad 33;
4. Detachment beacon, indicating that the sensor module 34 has been detached from the medical pad 33;
5. Clogged Pins beacon, indicating that at least one pogo pin 122 of the sensor module 34 is clogged;
6. Registration Request beacon, indicating that the sensor module 34 is received within a cradle 146 of the network station 36, requesting registration with the system; and
7. Roll over beacon, indicating that it is time for rolling over the relevant patient.

Figure 42:
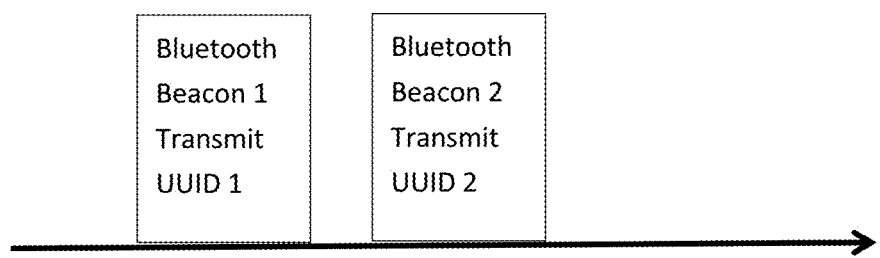
FIG. 42 shows schematically a method of sending two consecutive beacons.

In some broadcast messages, one beacon is not enough to carry all information; two beacons are needed. However, the basic nature of Bluetooth® Low Energy beacon is such that two consecutive beacons with the same universally unique identifier (UUID) will be duplicate filtered out. To overcome this, and as shown in FIG. 42, a novel method is devised to send out two consecutive beacons of two different sets of content, with two different UUIDs.

Figure 43:
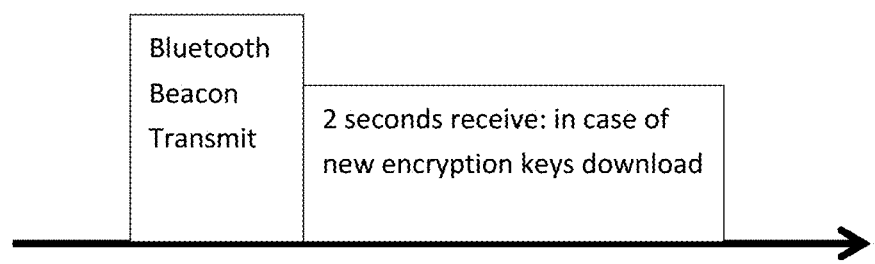
FIG. 43 shows schematically a method of allowing downloading of new encryption keys by the sensor module.

For encryption key download, also using Bluetooth® Low Energy beacon, by the bridge (network station 36), a special design is needed because the sensor module 34 are not normally listening, in order to conserve battery life. As shown in FIG. 43, a novel method is employed where the sensor module 34 changes to listening mode for 2 seconds after normal beacon to allow periodic downloading of new encryption key. The beacon containing the encryption key will be broadcasted in the 2 seconds after the normal Keep Alive beacon or the Wetness beacon.

To allow for easy expansion, User Datagram Protocol (UDP) protocol is used in the network exchange between the network stations 36 and the Cloud Frontend server 38. To protect the data, the full data packet from the network station 36 is encrypted. The encryption key is configurable to have a periodic update. A novel key update scheme is employed that allows the Cloud Frontend server 38 to update not only the encryption key of the network stations 36, but also that of the sensors 34.

Figure 44:
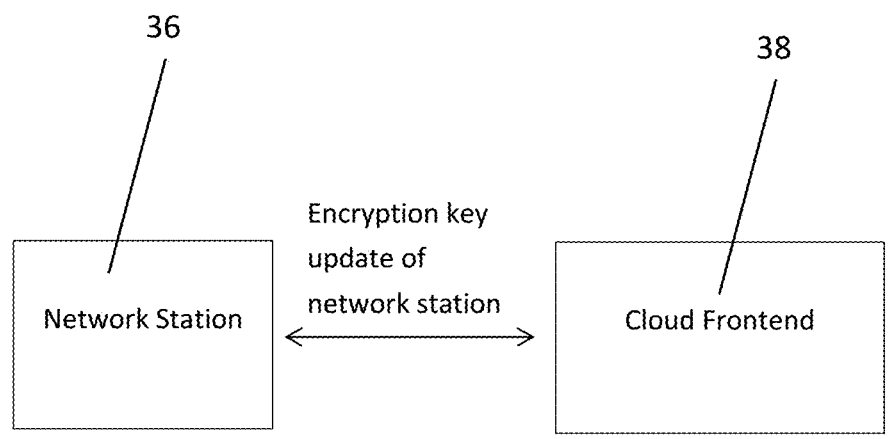
FIG. 44 shows update of network station encryption key.
Figure 45:
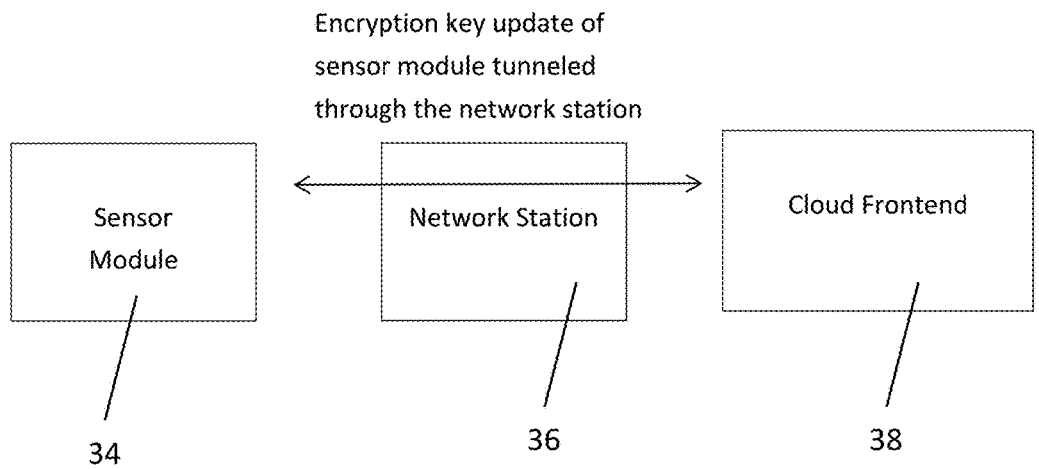
FIG. 45 shows update of sensor module encryption key.
Figure 46:
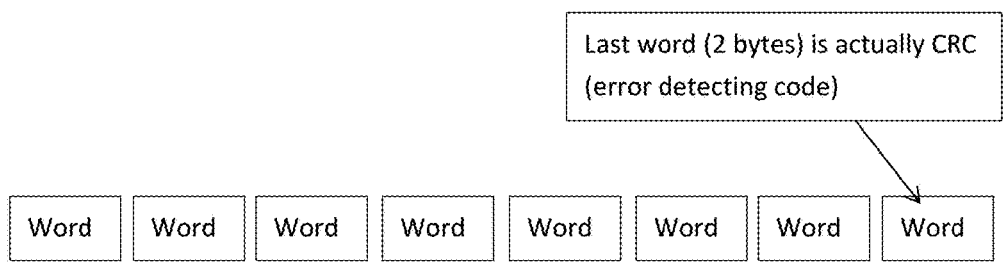
FIG. 46 shows a sensor module encryption key format.

As shown in FIG. 44, there is an encryption key between the network station 36 and the Cloud Frontend server 38. There is also an encryption key between the sensor module 34 and the Cloud Frontend server 38. However, the network station 36 does not know what the encryption key of the sensor module 34 is. In other words, the information is tunneled through the network station 36, as shown in FIG. 45. This ensures maximum security where compromising the network station 36 will not get the critical wetness data.

A novel scheme is also employed where the 128 bit encryption key consists of 16 bits of cyclic redundancy check (CRC) code. This novel scheme allows the key to be broadcasted out and be distributed to the sensor module 34 directly. The sensor module 34 uses the previous key to decrypt it first and then checks the CRC to make sure it is a valid key. This is extremely important because any bit error will cause a wrong key to be downloaded to the sensor module 34, and with all subsequent keys to be wrong and undecipherable by the Cloud Frontend server 38.

Figure 47:
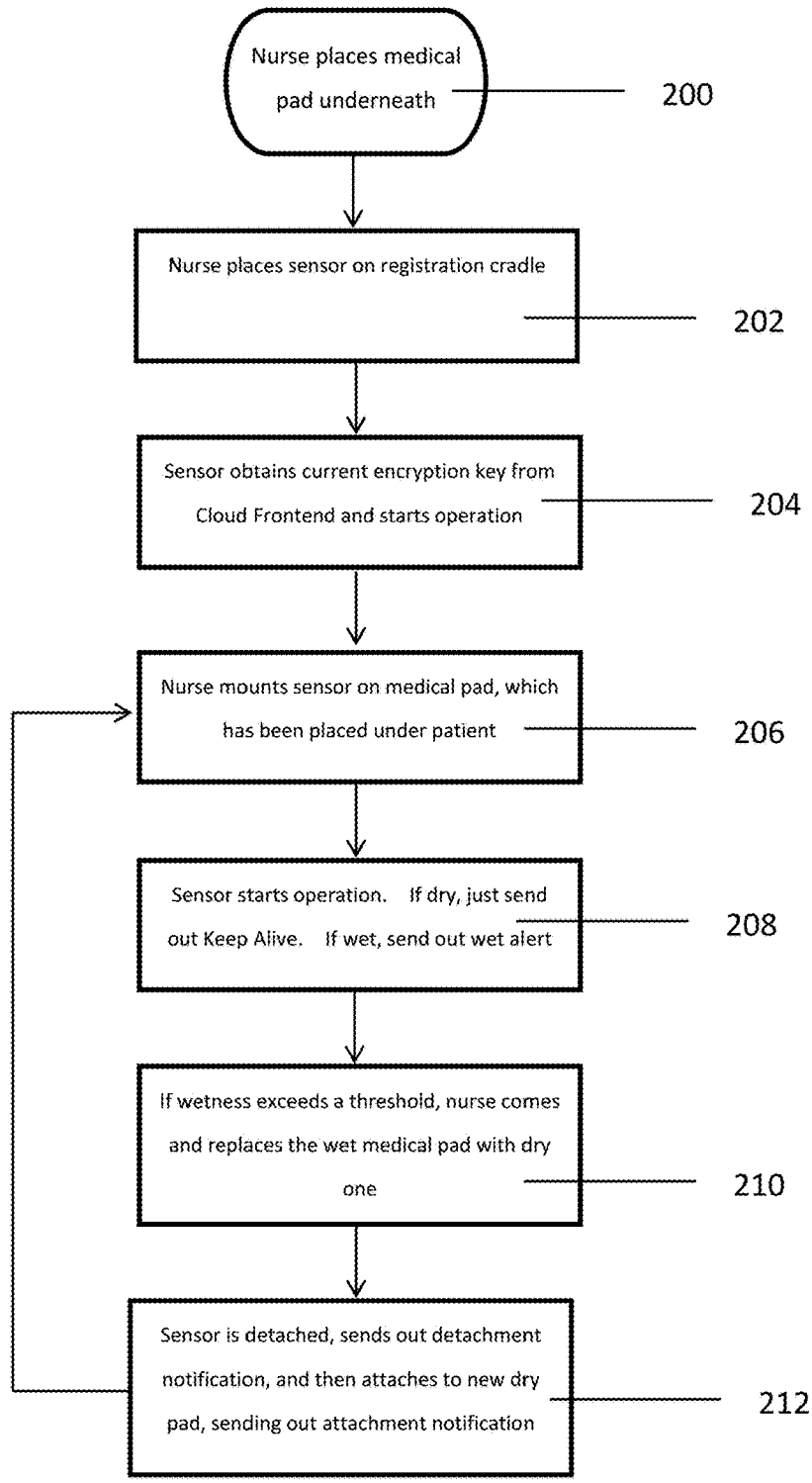
FIG. 47 shows a flow chart of operation of an active wetness reporting system according to the present invention.

FIG. 47 is a flowchart showing the operation of an active wetness reporting medical pad system according to the present invention. When a patient is admitted into a particular room, the nurse places (200) an active medical pad 33 (to which an active sensor module 34 is yet to be attached) according to the present invention on the bed to which the patient is assigned. The nurse then places (202) an active sensor module 34 on the registration cradle 146 of the network station 36. Once placed there, a registration sequence will kick off, with the information of the sensor module 34 sent by the network station 36 to the Cloud Frontend server 38. The Cloud Frontend server 38 then notifies the nurse station 42. The nurse then sees a request pop up on the nurse station 42 (a personal computer (PC), an iPAD® or other tablet devices). The nurse then type in the patient name, bed number, room number, and/or other related information. Then the nurse presses OK and Save. The nurse station application software (App) then notifies the Cloud Frontend server 38 the completion of this information. The actual patient information is not sent to the Cloud Frontend server 38. Therefore confidential and private information of the patient stays on the nurse station 42, without ever going to the Cloud Frontend server 38. Once the Cloud Frontend server 38 receives this completion notification, it then sends a registration OK plus the current encryption key to the network station 36, which then relays that information to the sensor module 34 (204). At that point the registration operation is completed.

The nurse then takes the sensor module 34 out from the registration cradle 146 and then mounts it on the medical pad 33 (206). Once there, the sensor module 34 will start monitoring the wetness of the medical pad 33 every thirty seconds. If the status of the medical pad 33 is dry, the sensor module 34 will send out Keep Alive beacon. If the wet status is anything other than dry, the sensor module 34 will broadcast a Wetness beacon (208), which will be picked up by one or more network stations 36 nearby, and that information will then be sent to the Cloud Frontend server 38. The Cloud Frontend server 38 will log the information, and then send the information to the Cloud Backend server 40 to do the wetness calculation. Once the Cloud Backend server 40 completes the calculation, it will send the wetness diagnosis result back to the Cloud Frontend server 38.

Once that wetness diagnosis is received, the Cloud Frontend server 38 will then send the information to the nurse station 42. The nurse station App will show the updated wetness. If a wetness result is received, the nurse station App will pop up a large warning window and the nurse must press the screen to acknowledge receipt. This receipt will be time- and date-stamped in the database. The nurse will then need to go and replace the medical pad 33 (210). As the nurse detaches the sensor module 34, the sensor module 34 will send out Detachment beacon. This detachment will be time- and date-stamped in the database. As the nurse removes the wet medical pad 33 and replaces a dry one on the bed, the nurse will attach the sensor module 34 to the medical pad 33. At the point of attachment, an Attachment beacon is also sent out by the sensor module 34 (212). This new pad attachment will be time- and date-stamped in the database. These two types of beacons, in the above mentioned sequence, will signal to the Cloud Frontend server 38 that the nurse has indeed replaced the medical pad 33.

If the medical pad 33 stays dry, the sensor module 34 will not send out Wetness beacon. However, the sensor module 34 will still send out a Keep Alive beacon periodically, with the period set to five minutes or other default time period configurable ex-factory. This will ensure the Cloud Frontend server 38 knows that the sensor module 34 still exists and is in normal operation. The Keep Alive beacon also contains the battery level. This battery level and keep alive status is then sent down to the nurse station App so that the nurse will know that the sensor module 34 is still working and its battery level is still acceptable.

Figure 48:
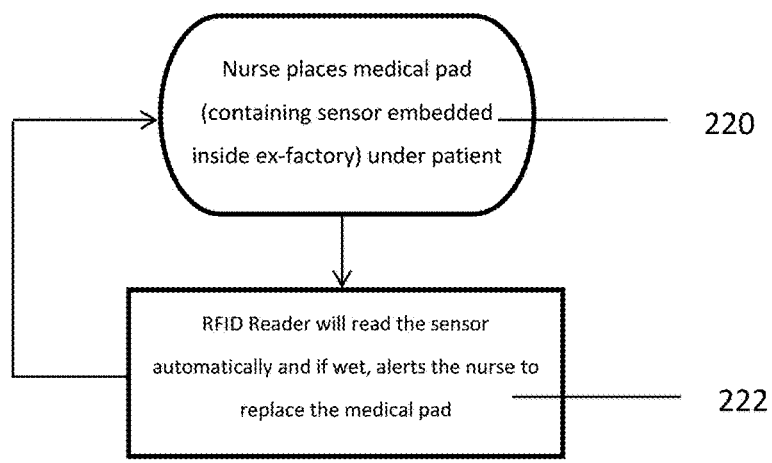
FIG. 48 shows a flow chart of operation of a passive wetness reporting system according to the present invention.

FIG. 48 is a flowchart showing the operation of a passive wetness reporting medical pad system according to the present invention. In this system, when a patient is admitted to the room, the nurse will, on a personal computer application software (App) on the nurse station 52, pair the patient name with the bed number to which the patient is assigned. In this passive system, the RFID reader 50 on the bed does not move. So the pairing is very simple: bed to patient name. Again, this information stays on the nurse station 54 and is never sent out. So privacy and confidentiality is maintained.

The passive medical pad 47 is placed on the bed (220). Note that the passive medical pad 47 already contains the wetness detection circuit and the sensor module 46. For the passive system, the medical pad 47 and the sensor module 46 are already mated together ex-factory. The nurse does not have to do any snapping on of the sensor module 46. When the medical pad 47 is wet and needs to be thrown away, the nurse simply throws away the whole medical pad 47 and replaces with a new and dry one. In terms of changeover, the passive solution is actually simpler.

The RFID reader 50 periodically energizes and reads the RFID tag 116 in the sensor module 46, and then obtains the raw wetness information, via the ultra-thin antenna 48 underneath the mattress. This information is then passed to the intelligent processor 50 and analyzed. The resulting wetness status, only wet or dry, will be sent to the nurse station 54 personal computer (PC) or iPAD® or Android® Pad. The nurse will be alerted by the user interface and will then need to replace the wet medical pad (222).

Figure 49:
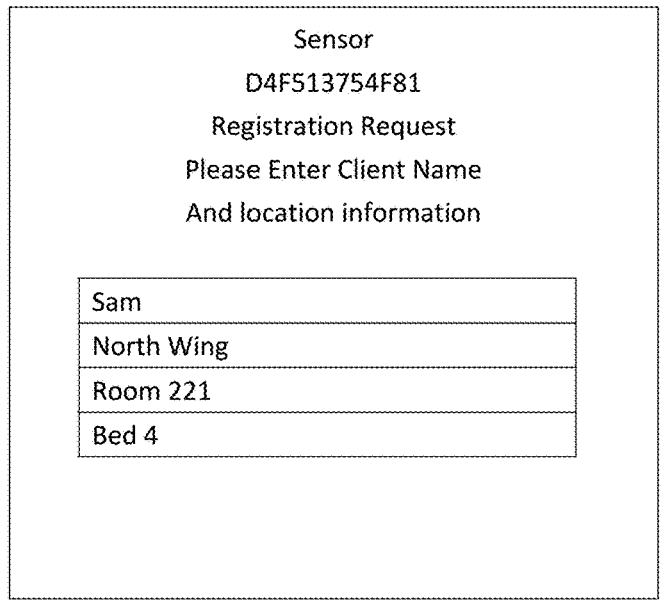
FIG. 49 shows an exemplary screen display during pairing of the identity (ID) of a sensor module with patient name in the active wetness reporting system according to the present invention.

In the case of the active wetness reporting medical pad system, a Nurse Application (being a piece of software) is connected to the Cloud Frontend server 38 to accept wetness alert and registration request, and then to allow the nurse to map that to the actual patient name, as shown in FIG. 49. The patient name may just be typed in by the nurse, or, with permission of the hospital authorities, obtained by accessing the hospital patient information system.

Figure 50:
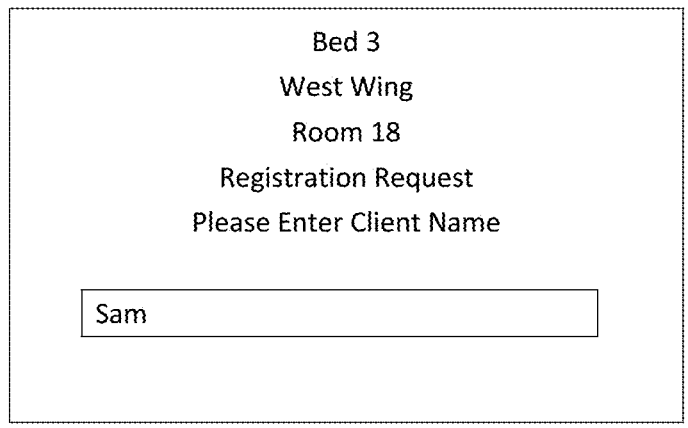
FIG. 50 shows an exemplary screen display during pairing of bed number with patient name in the passive wetness reporting system according to the present invention.

In the case of the passive wetness reporting medical pad system, a Nurse Application (being a piece of software) on the nurse station PC (or an iPAD®, Android® Pad or Windows® Pad) used by the nurse connected to the intelligent processor 50 to accept wetness alert and registration request, and also allow the nurse to pair that to the actual patient name. Again, as shown in FIG. 50, the patient name may just be typed in by the nurse, or, with permission of the hospital authorities, obtained by accessing the hospital patient information system.

Figure 51:
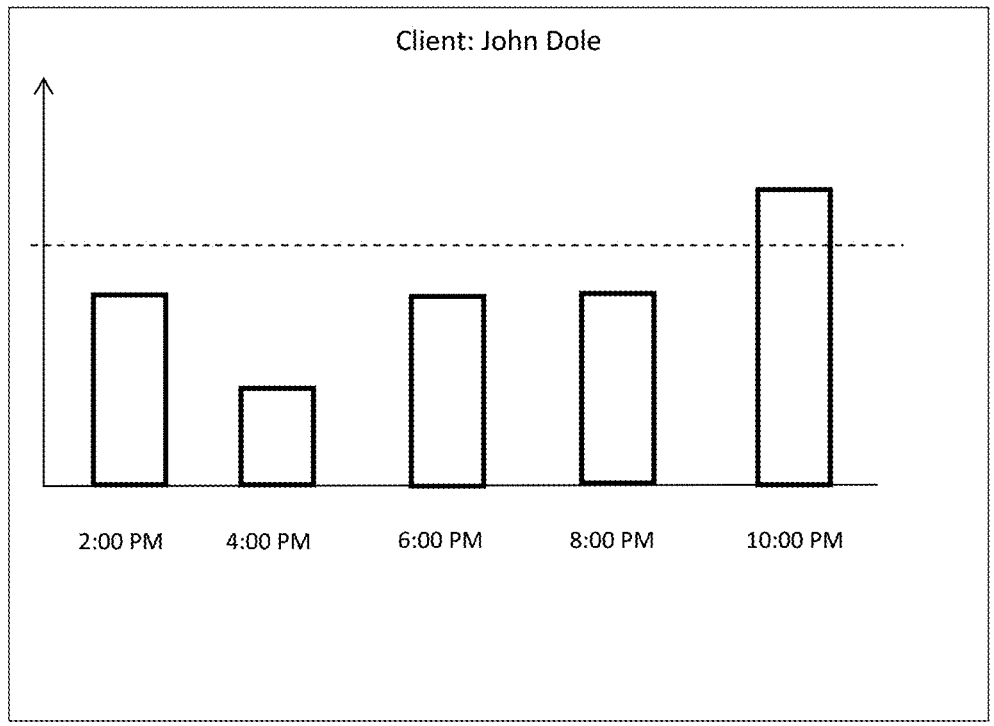
FIG. 51 shows an exemplary screen display showing a patient's statistics of wetness over time.

In both active and passive systems, and as shown in FIG. 51, the Nurse Application also provides statistics of nurse actions and provides reminder notification services to nurses to do regular roll-over of patients to prevent bed sores, as shown in FIG. 52. Documentation of all events and nurse actions, as shown in FIG. 53, provides clear evidence of procedural adherence by the medical facility to their standard of care protocol, in case of any regular audit or special audit (usually caused by complaints lodged by patients or patient families) or even legal actions.

Figure 54:
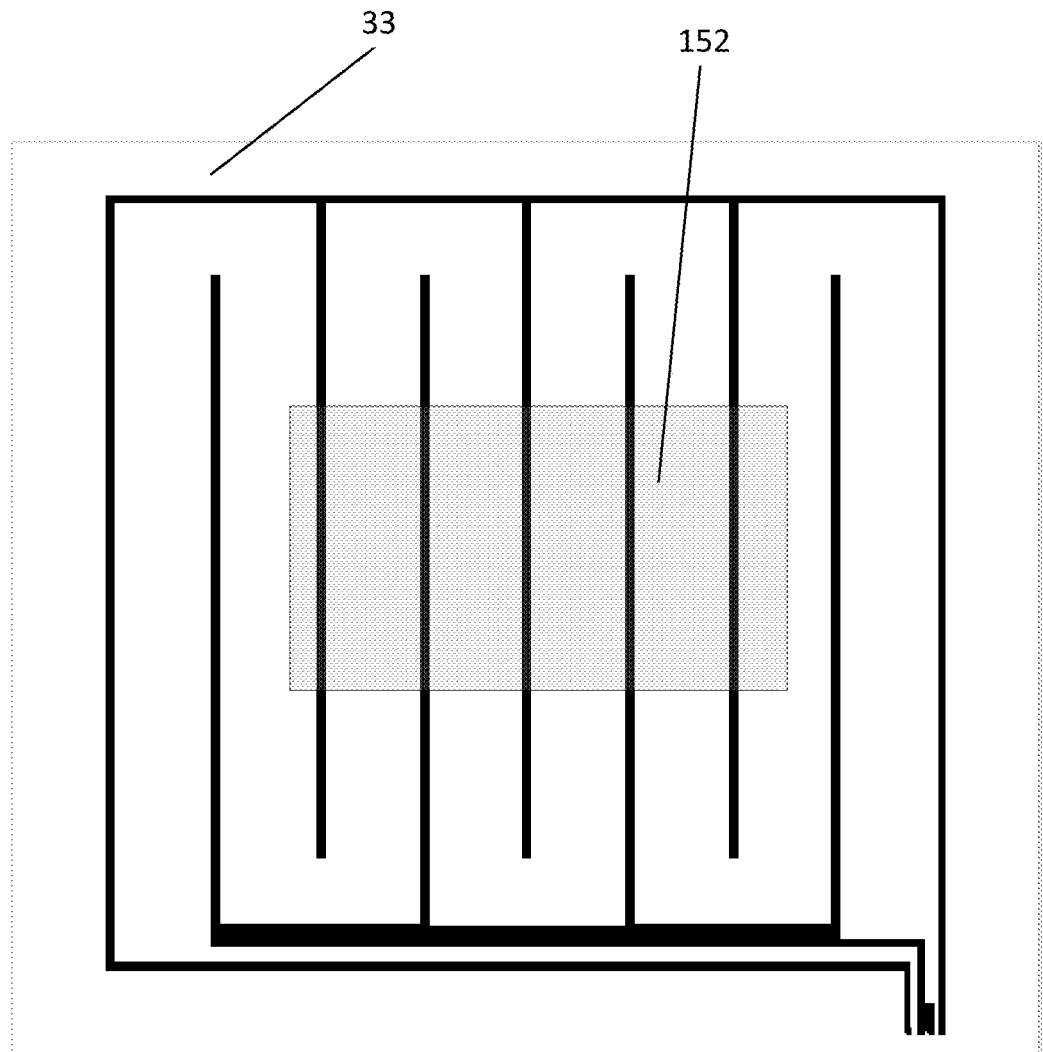
FIG. 54 shows a medical pad according to the present invention with a pressure sensor.

As shown in FIG. 54, a pressure sensor 152 may also be placed in the medical pad 33 to detect the presence of a patient lying thereon. When the patient is rolled over by the nurse, the pressure sensor 152 will sense the reduction of pressure. Such a pressure sensor 152 is only applicable to an active medical pad 33 and thus an active wetness reporting system because the pressure sensor 152 needs to be tracked in very high frequency to capture the time when the nurse is rolling the patient over and back. A nurse will usually roll the patient over for ten seconds. So the pressure sensor 152 tracking interval must be less than ten seconds. A typical pressure sensor 152 suitable for application in the medical pad 33 may be a thin film pressure sensor.

Figure 55:
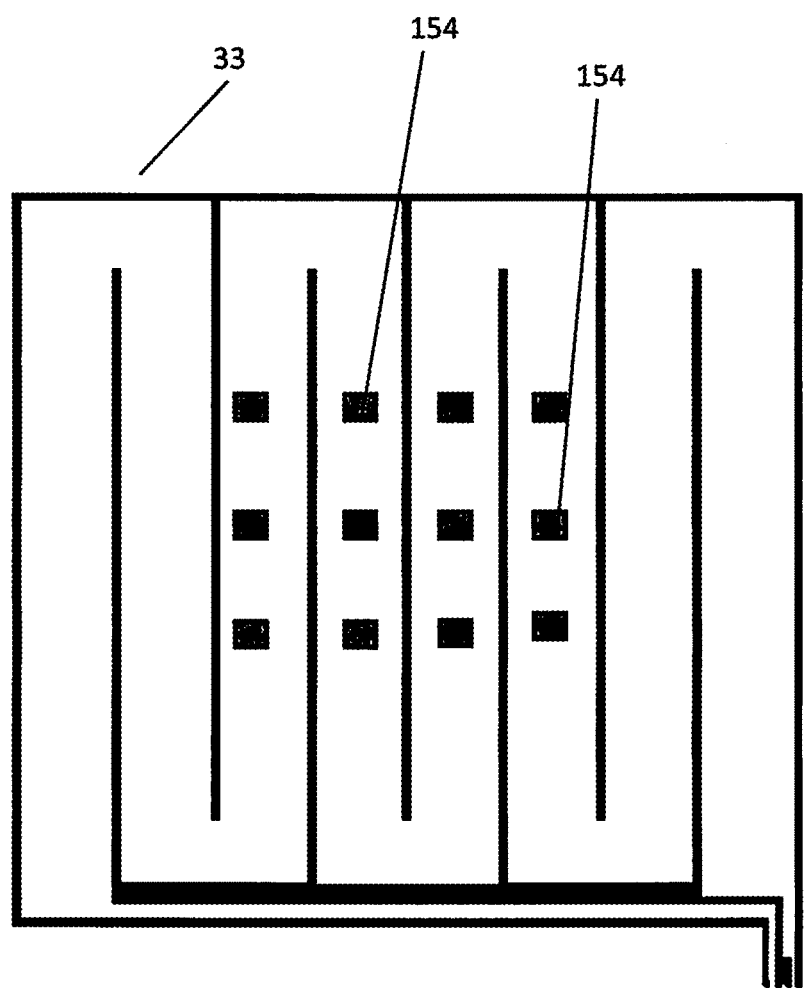
FIG. 55 shows a medical pad according to the present invention with a light sensor.

As shown in FIG. 55, one or more light sensors 154 may also be placed in the medical pad 33 to detect the presence of a patient lying thereon. When the patient is rolled over by a nurse, and if the roll over action is applied on the patient only without including the medical pad 33, the light sensor 154 will sense the light of the room. Light sensor 154 is only applicable to an active medical pad 33, and thus an active wetness reporting system because the light sensor 154 needs to be tracked in very high frequency to capture the time when the nurse is rolling the patient over and back. A nurse will usually roll the patient over for ten seconds. So the light sensor 154 tracking interval must be less than ten seconds.

Figure 56:
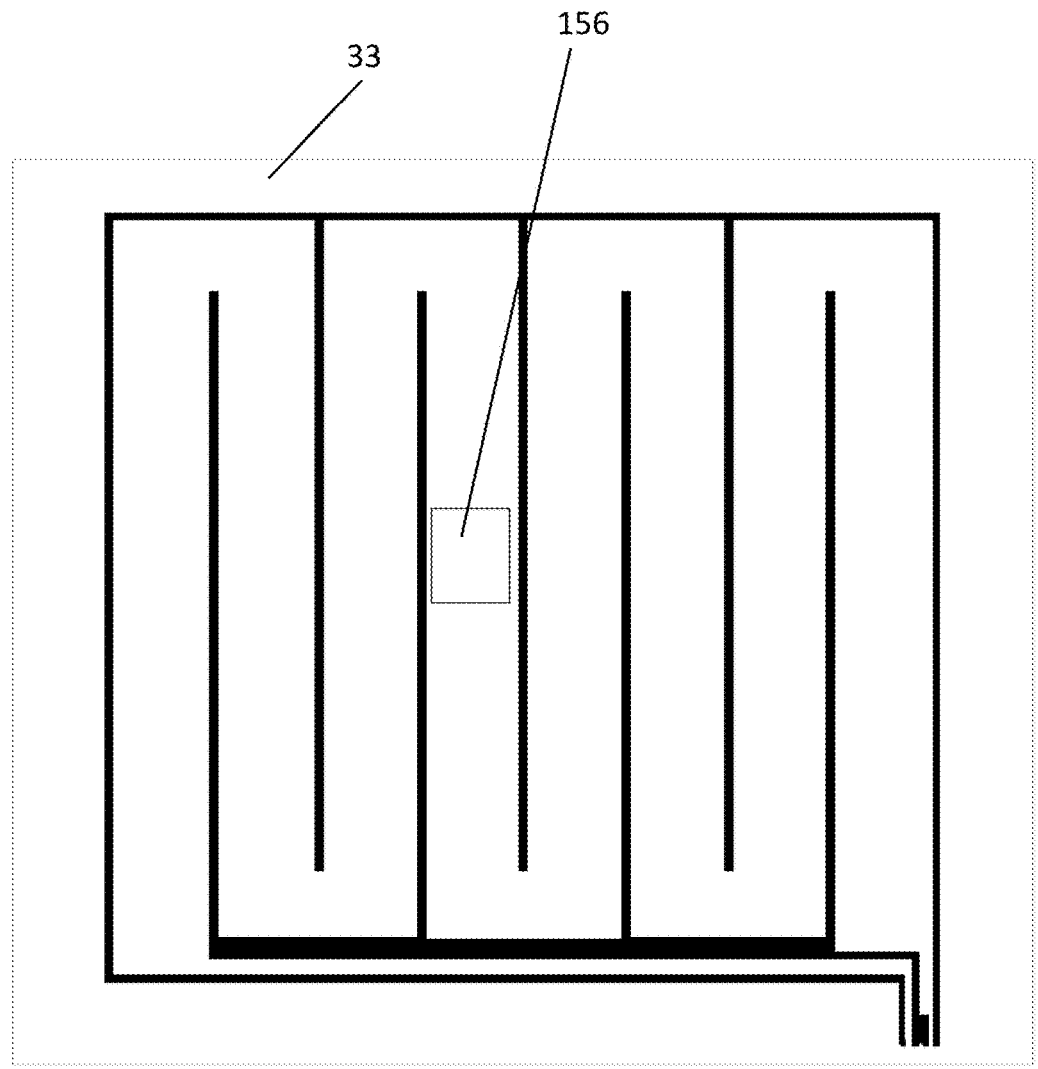
FIG. 56 shows a medical pad according to the present invention with a gas sensor.

As shown in FIG. 56, a gas sensor 156, for example hydrogen sulfide (H$_2$S) sensor, may also be placed in the medical pad 33 to detect the emission of gas from the patient lying thereon. A gas sensor 156 is only applicable to an active medical pad 33 and thus an active wetness reporting system because the gas sensor 156 needs to be tracked in very high frequency to capture the time when the gas is emitted. So the gas sensor 156 tracking interval must be less than ten seconds. A typical gas sensor 156 suitable for application in the medical pad 33 may be a thin film gas sensor.

Figure 57:
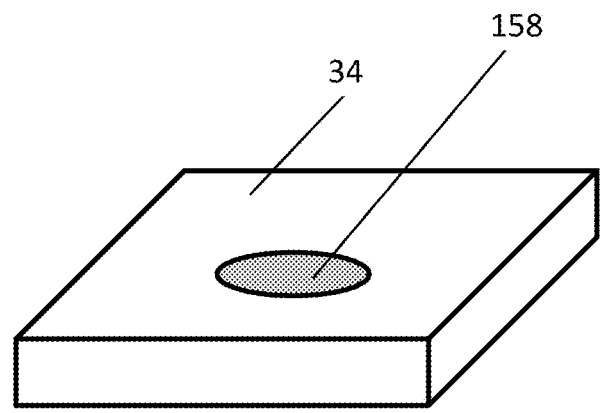
FIG. 57 shows a button on the sensor module.

As shown in FIG. 57, a button 158 may be included in the wetness detection sensor module 34 for the nurse to signal that a patient roll-over action has been done. After the nurse rolls the patient, the nurse is to press the button 158 on the sensor module 34.

Figure 58:
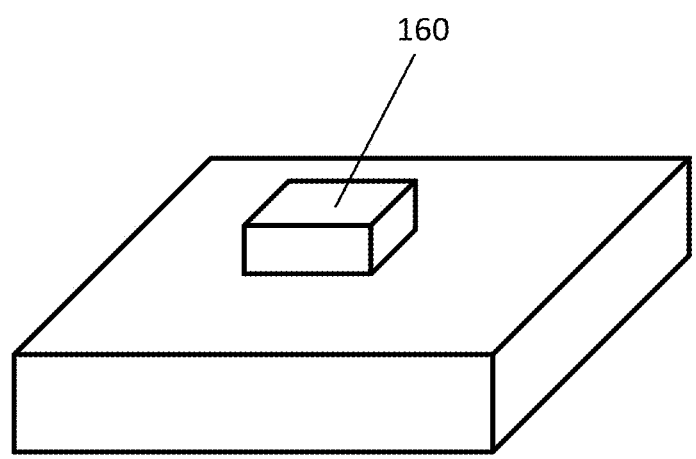
FIG. 58 shows a posture sensor associated with the medical pad.

As shown in FIG. 58, a posture sensor 160 may also be releasably mounted on the patient to signal that the patient has rolled over. This sensor module 34 would send out, via Bluetooth® as well, the roll-over induced posture change of the patient.

The time sequence of detachment of the sensor 34 from and subsequent attachment of the sensor module 34 to the medical pad 33 may be used for marking the time at which the nurse performs the roll over action on the patient. This action time sequence may be detected, stored and analyzed by the system to denote the time of occurrence of a roll over event. The documentation of this roll over event will become a medical record to allow the hospitals and facilities to follow and manage the roll over service.

The time of detachment of the sensor 34 from the medical pad 33 may be used as the time at which a nurse enters the ward/room or starts attending to the patient, and the time of attachment of the sensor 34 to the medical pad may be used as the time at which the nurse leaves the ward/room or ends attending to the patient. The documentation of the time interval between these two points of time will become a medical record to allow the hospitals and facilities to follow and manage the nurse attention time.

The nurse may also carry a Bluetooth® sensor or badge so that wireless signal emitted from the Bluetooth® sensor/badge will also be captured by the network station 36, and the proximity of the Bluetooth® sensor/badge will give a certain received signal strength exceeding a preset level, and hence the presence of the nurse in the ward/room or near the patient can be deduced. When the received signal strength falls below the preset level, the nurse is deduced to be away from the ward/room. The time at which the nurse's presence is deduced, the time at which the nurse's absence is deduced, and the time interval during which the nurse is present in a ward/room or near the patient can be documented and becomes a medical record to allow the hospitals or facilities to follow and manage the nurse attention time.

It should be understood that the above only illustrates examples whereby the present invention may be carried out, and that various modifications and/or alterations may be made thereto without departing from the spirit of the invention.

It should also be understood that certain features of the invention, which are, for clarity, described in the context of separate embodiments, may be provided in combination in a single embodiment. Conversely, various features of the invention which are, for brevity, described in the context of a single embodiment, may also be provided separately or in any appropriate sub-combinations.

The invention claimed is:

1. A wetness reporting pad including:
   a piece of substrate with a major surface and an electric circuit on said major surface,
   a sensor connected with said electric circuit for measuring the electrical resistance of said electric circuit, and
   a data transmitter for receiving results of said measuring from said sensor for wireless transmission,
   wherein said electric circuit includes a first electrically conductive line with a first terminal and a second electrically conductive line with a second terminal, each said electrically conductive line being in the shape of a comb and interlocking with each other, and
   wherein at least said first electrically conductive line has a first section and a second section which are of different widths.

2. The wetness reporting pad of claim 1, wherein said first electrically conductive line has a third section with a width different from the width of said first section and the width of said second section.

3. The wetness reporting pad of claim 1, wherein said first electrically conductive line and said second electrically conductive line comprise conductive ink printed on said substrate.

4. The wetness reporting pad of claim 1, wherein said first electrically conductive line and said second electrically conductive line comprise electrically conductive threads sewn onto said substrate.

5. The wetness reporting pad of claim 4, wherein said electrically conductive threads are covered at least in part by yarn.

6. A wetness reporting pad including:
   a piece of substrate with a major surface and an electric circuit on said major surface,
   a sensor connected with said electric circuit for measuring the electrical resistance of said electric circuit, and
   a data transmitter for receiving results of said measuring from said sensor for wireless transmission,
   wherein said sensor and said data transmitter are comprised in an integrated circuit (IC),
   further including a third terminal connecting with said second electrically conductive line via a calibration conductive line, allowing electrical resistance of said electric circuit to be measured for calibration purpose.

7. A wetness reporting pad including:
   a piece of substrate with a major surface and an electric circuit on said major surface,
   a sensor connected with said electric circuit for measuring the electrical resistance of said electric circuit, and
   a data transmitter for receiving results of said measuring from said sensor for wireless transmission,
   wherein said sensor and said data transmitter are comprised in an integrated circuit (IC),
   wherein said IC is comprised in a sensor module which is releasably engageable with said substrate,
   wherein said sensor module includes a plurality of waterproof spring-loaded pogo pins which, when said sensor module is engaged with said substrate, electrically connect with said electric circuit on said major surface of said substrate, and wherein said sensor is adapted to measure the electrical resistance of each of said waterproof spring-loaded pogo pins.

8. A wetness reporting pad including:
a piece of substrate with a major surface and an electric circuit on said major surface,
a sensor connected with said electric circuit for measuring the electrical resistance of said electric circuit, and
a data transmitter for receiving results of said measuring from said sensor for wireless transmission,
wherein said sensor and said data transmitter are comprised in an integrated circuit (IC), and
wherein said sensor is adapted to measure the electrical resistance of said electric circuit in a pulsed manner.

9. A wetness reporting system including at least one wetness reporting pad according to any one of claim 1, 6, 7 or 8, further including at least one network station and at least one server,
wherein said at least one network station is wirelessly connected with said wetness reporting pad for data communication,
wherein said at least one network station is wirelessly connected with said server for data communication, and
wherein a sensor module comprising said sensor and said data transmitter is releasably physically engageable with said network station.

10. The system of claim 9, wherein when said sensor module is engaged with said network station, said sensor module is physically registrable or re-registrable with said system.

11. A wetness reporting system including at least one wetness reporting pad, at least one RFID reader and at least one antenna,
wherein said wetness reporting pad includes:
a piece of substrate with a major surface and an electric circuit on said major surface,
a sensor connected with said electric circuit for measuring the electrical resistance of said electric circuit, and
a data transmitter for receiving results of said measuring from said sensor for wireless transmission,
wherein said antenna has a leaky wave travelling wave mechanism,
wherein radio frequency wave leaks out from a top surface of a parallel plate travelling wave waveguide of said antenna,
wherein said top surface comprises a crossed mesh of conductive aluminum material, and
wherein said parallel plate travelling wave waveguide of said antenna has as its excitation a sideway approaching coaxial cable with an external connector grounded to a metal back of said antenna.

12. A method of reporting wetness of a subject, including steps:
(a) positioning an electric circuit beneath said subject,
(b) measuring the electrical resistance of said electric circuit,
(c) wirelessly transmitting data indicative of the electrical resistance of said electric circuit, and
(d) determining, on the basis of said data, whether the subject is wet,
wherein said step (b) is carried out in a pulsed manner.

13. A method of reporting wetness of a subject, including steps:
(a) positioning an electric circuit beneath said subject,
(b) measuring the electrical resistance of said electric circuit,
(c) wirelessly transmitting data indicative of the electrical resistance of said electric circuit,
(d) determining, on the basis of said data, whether the subject is wet, and
(e) sensing and storing the time at which a sensor module is detached from a wetness reporting pad and the time at which said sensor module is attached to a wetness reporting pad.

14. A method of reporting wetness of a subject, including steps:
(f) positioning an electric circuit beneath said subject,
(g) measuring the electrical resistance of said electric circuit,
(h) wirelessly transmitting data indicative of the electrical resistance of said electric circuit, and
(i) determining, on the basis of said data, whether the subject is wet,
wherein said sensor and said data transmitter are comprised in an integrated circuit,
wherein said IC is comprised in a sensor module which is releasably engageable with said substrate, and
wherein said sensor module includes a plurality of waterproof spring-loaded pogo pins which, when said sensor module is engaged with said substrate, electrically connect with said electric circuit on said major surface of said substrate,
further including a step (j) of measuring the electrical resistance of each of said plurality of waterproof spring-loaded pogo pins for detection of clogging of said waterproof spring-loaded pogo pins.

15. A method of calibrating a wetness reporting pad:
wherein said wetness reporting pad includes a piece of substrate with a major surface and an electric circuit on said major surface, a sensor connected with said electric circuit for measuring the electrical resistance of said electric circuit, and a data transmitter for receiving results of said measuring from said sensor for wireless transmission,
wherein said electric circuit includes a first electrically conductive line with a first terminal and a second electrically conductive line with a second terminal, each said electrically conductive line being in the shape of a comb and interlocking with each other, and
wherein said electric circuit further includes a third terminal connecting with said second electrically conductive line via a calibration conductive line,
said method including a step (r) of measuring the electrical resistance of said calibration conductive line.

16. The method of claim 15, further including a step (s) of measuring the electrical resistance of said calibration conductive line regularly.

17. The method of claim 16, wherein said step (s) is carried out every ten minutes.

18. The method of claim 15, wherein said step (r) is carried out every time said data transmitter broadcasts a Keep Alive beacon.

19. The method of claim 15, wherein said step (r) is carried out every time a sensor module comprising said sensor and said transmitter is attached to a wetness reporting pad.

20. The method of claim 15, further including a step (t) of sending data of said measurement in said step (r) to a server for storage.

* * * * *